(12) United States Patent
Agustsson et al.

(10) Patent No.: US 11,627,653 B2
(45) Date of Patent: *Apr. 11, 2023

(54) COMPACT LINEAR ACCELERATOR WITH ACCELERATING WAVEGUIDE

(71) Applicant: RadiaBeam Technologies, LLC, Santa Monica, CA (US)

(72) Inventors: Ronald Agustsson, Venice, CA (US); Robert Berry, Los Angeles, CA (US); Salime Boucher, Santa Monica, CA (US); Josiah Hartzell, Santa Monica, CA (US); Sergey Kutsaev, Santa Monica, CA (US); Jacob McNevin, Los Angeles, CA (US); Avinash Verma, Chatsworth, CA (US)

(73) Assignee: RadiaBeam Technologies, LLC, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/099,605

(22) Filed: Nov. 16, 2020

(65) Prior Publication Data

US 2021/0219413 A1 Jul. 15, 2021

Related U.S. Application Data

(63) Continuation of application No. 16/675,058, filed on Nov. 5, 2019, now Pat. No. 10,880,985, which is a
(Continued)

(51) Int. Cl.
*H05H 9/02* (2006.01)
*A61N 5/10* (2006.01)
(Continued)

(52) U.S. Cl.
CPC ............. *H05H 9/02* (2013.01); *A61N 5/1045* (2013.01); *G21K 1/046* (2013.01); *H05H 9/04* (2013.01); *H05H 9/048* (2013.01); *G21K 1/02* (2013.01)

(58) Field of Classification Search
CPC ............ H05H 9/02; H05H 9/04; H05H 9/048; A61N 5/1045; G21K 1/046; G21K 1/02
(Continued)

(56) References Cited

U.S. PATENT DOCUMENTS 3,796,906 A * 3/1974 Henry-Bezy ............ H05H 9/00
315/5.41
4,107,617 A 8/1978 Tran
(Continued)

FOREIGN PATENT DOCUMENTS

CN 202095170 U 12/2011
CN 10261225161 3/2015
(Continued)

OTHER PUBLICATIONS

Smirnov A V, et al.; "Multi-cell disk-and-ring tapered structure for compact RF linacs", Nuclear Instruments & Methods in Physics Research. Section A. Elsevier BV * North-Holand, NL, Jun. 4, 2016, vol. 830, pp. 294-302.
(Continued)

*Primary Examiner* — Srinivas Sathiraju
(74) *Attorney, Agent, or Firm* — Knobbe Martens Olson & Bear LLP

(57) ABSTRACT

A linear accelerator head for use in a medical radiation therapy system can include a housing, an electron generator configured to emit electrons along a beam path, and a microwave generation assembly. The linear accelerator head may include a waveguide that is configured to contain a standing or travelling microwave. The waveguide can
(Continued)

include a plurality of cells that are disposed adjacent one another, wherein each of the plurality of cells may define an aperture configured to receive electrons therethrough. The linear accelerator head can further include a converter and a primary collimator.

20 Claims, 18 Drawing Sheets

Related U.S. Application Data continuation of application No. 16/276,323, filed on Feb. 14, 2019, now Pat. No. 10,609,809, which is a continuation of application No. 15/933,257, filed on Mar. 22, 2018, now Pat. No. 10,212,800.

(60) Provisional application No. 62/476,630, filed on Mar. 24, 2017.

(51) Int. Cl.
 G21K 1/04 (2006.01)
 H05H 9/04 (2006.01)
 G21K 1/02 (2006.01)

(58) Field of Classification Search
 USPC ............................................................. 315/505
 See application file for complete search history.

(56) References Cited

U.S. PATENT DOCUMENTS

| | | | |
|---|---|---|---|
| 5,107,839 A * | 4/1992 | Houdek | A61N 5/1049 600/417 |
| 5,757,146 A * | 5/1998 | Carder | H05H 9/00 315/505 |
| 6,331,194 B1 * | 12/2001 | Sampayan | H05H 7/00 29/25.03 |
| 6,448,722 B1 | 9/2002 | Yu et al. | |
| 7,046,765 B2 | 5/2006 | Wong et al. | |
| 7,400,096 B1 | 7/2008 | Foster et al. | |
| 7,764,324 B2 | 7/2010 | Andonian et al. | |
| 8,107,589 B2 | 1/2012 | Sakurai et al. | |
| 8,143,816 B2 | 3/2012 | Clayton et al. | |
| 8,148,922 B2 | 4/2012 | Cleland et al. | |
| 8,947,115 B2 | 2/2015 | Rosenzweig et al. | |
| 9,023,765 B1 | 5/2015 | Rimmer et al. | |
| 9,750,122 B1 * | 8/2017 | Elizondo-Decanini | H05H 5/06 |
| 9,847,205 B2 | 12/2017 | Sherman et al. | |
| 9,867,271 B2 | 1/2018 | Saverskiy | |
| 9,913,360 B1 | 3/2018 | Antipov et al. | |
| 10,212,800 B2 * | 2/2019 | Agustsson | G21K 1/046 |
| 10,367,508 B1 * | 7/2019 | Miller | H01J 35/025 |
| 10,609,809 B2 * | 3/2020 | Agustsson | G21K 1/046 |
| 10,880,985 B2 * | 12/2020 | Agustsson | G21K 1/046 |
| 10,932,354 B2 * | 2/2021 | Agustsson | H05H 9/00 |
| 2004/0183486 A1 * | 9/2004 | Goldstein | H05G 2/00 315/503 |
| 2004/0195971 A1 * | 10/2004 | Trail | H01J 35/00 315/5.41 |
| 2004/0258189 A1 * | 12/2004 | Norman | G01V 5/0091 376/154 |
| 2007/0138980 A1 * | 6/2007 | Sanders | H05H 9/00 315/505 |
| 2008/0129203 A1 * | 6/2008 | Agustsson | H01J 23/005 315/5 |
| 2010/0059665 A1 * | 3/2010 | Sampayan | H05H 9/00 977/762 |
| 2011/0188638 A1 * | 8/2011 | Treas | H05H 7/02 313/363.1 |
| 2011/0290379 A1 * | 12/2011 | Murokh | H01F 1/053 148/559 |
| 2012/0081041 A1 | 4/2012 | Wah-Kwan et al. | |
| 2013/0163707 A1 | 6/2013 | Habs et al. | |
| 2013/0181637 A1 * | 7/2013 | Joshkin | H05H 9/005 315/505 |
| 2015/0057484 A1 | 2/2015 | Amaldi | |
| 2015/0230326 A1 * | 8/2015 | Botto | H05G 2/00 315/505 |
| 2015/0338545 A1 | 11/2015 | Arodzero | |
| 2017/0099724 A1 * | 4/2017 | Tajima | H05G 2/00 |
| 2017/0265292 A1 * | 9/2017 | Mishin | H05H 9/02 |
| 2018/0279461 A1 * | 9/2018 | Agustsson | H05H 9/048 |
| 2019/0320523 A1 * | 10/2019 | Agustsson | G21K 1/046 |
| 2020/0068699 A1 * | 2/2020 | Kutsaev | H05H 9/044 |
| 2020/0092979 A1 * | 3/2020 | Agustsson | H05H 9/02 |
| 2021/0204389 A1 * | 7/2021 | Agustsson | H05H 9/02 |
| 2022/0039246 A1 * | 2/2022 | Agustsson | H05H 7/18 |
| 2022/0223778 A1 * | 7/2022 | Kutsaev | G06N 10/00 |

FOREIGN PATENT DOCUMENTS

| | | |
|---|---|---|
| CN | 105555009 A | 5/2016 |
| EP | 1419799 A1 | 5/2004 |
| EP | 2421006 A1 | 2/2012 |

OTHER PUBLICATIONS

Kutsaev Sergery V, et al., "Electron linac with deep energy control for Adaptive Rail Cargo Inspection System", 2015 IEEE Nuclear Science Symposium and Medical Imaging Conference, Oct. 31, 2015, pp. 1-7.

Hoag H, et al., "Accelerator structure development for NLC", Particle Accelerator Confernce, Washington DC USA May 20, 1993, New York NY USA May 17, 1993, pp. 907-909.

Schonberg R G, et al., "Portable X-Band Linear Accelerator Systems", IEEE Transactions On Nuclear Science, IEEE Service Center, New York NY USA Oct. 1, 1985, vol. NS-32, No. 5, pp. 3234-3236.

Owen R D, "Portable linear accelerators for X-ray and electron-beam applications in civil engineering", NDT & E International, Butterworth-Heinemann, Oxford GB Dec. 1, 1998, vol.31, No.6, pp. 401-409.

S Boucher, et al., "Compact, Inexpensive X-Band Linacs as Radioactive Isotope Source Replacements", Jul. 17, 2012.

* cited by examiner

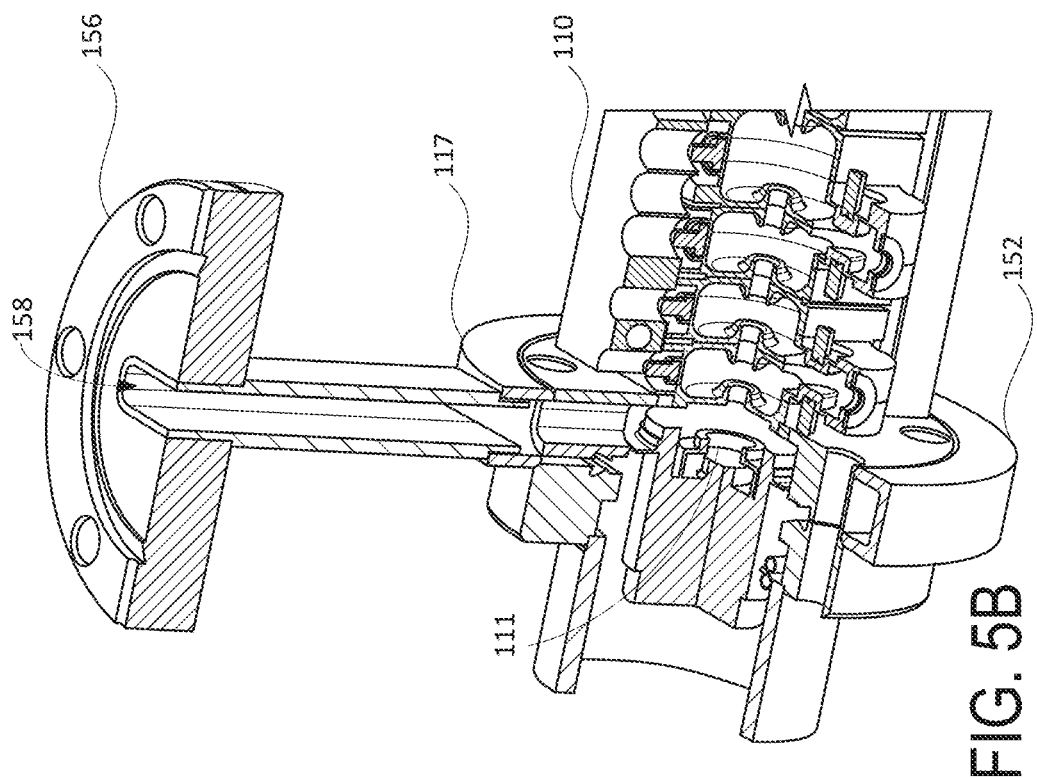
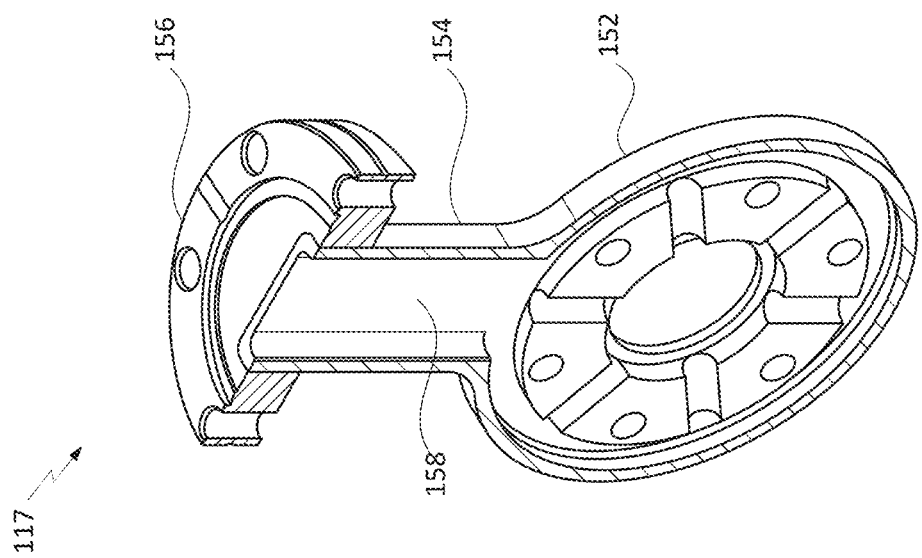
FIG. 5A
FIG. 5B

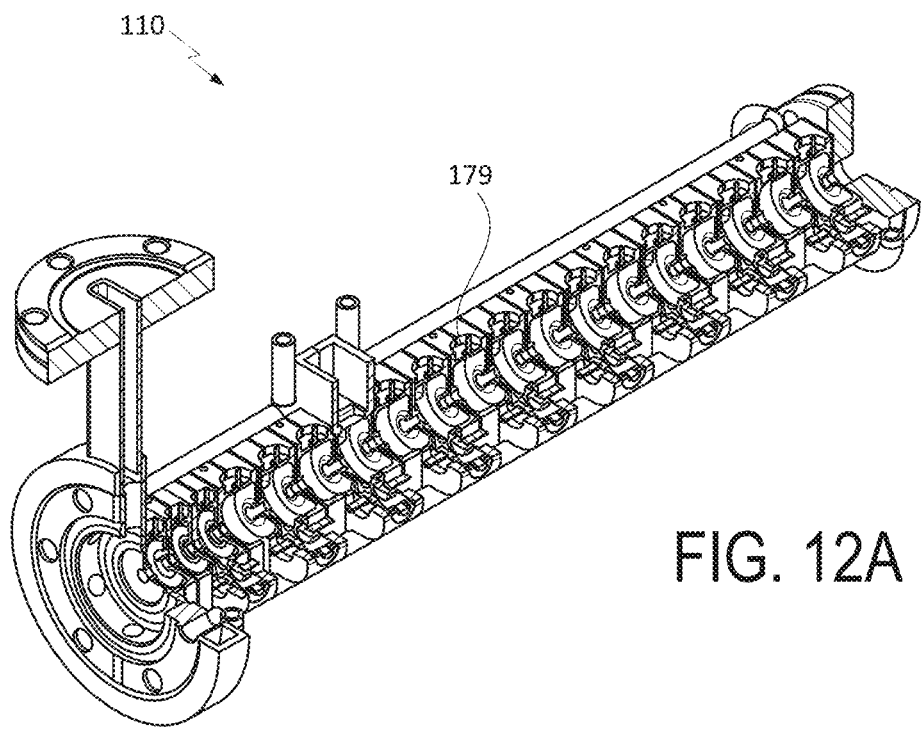
FIG. 12A
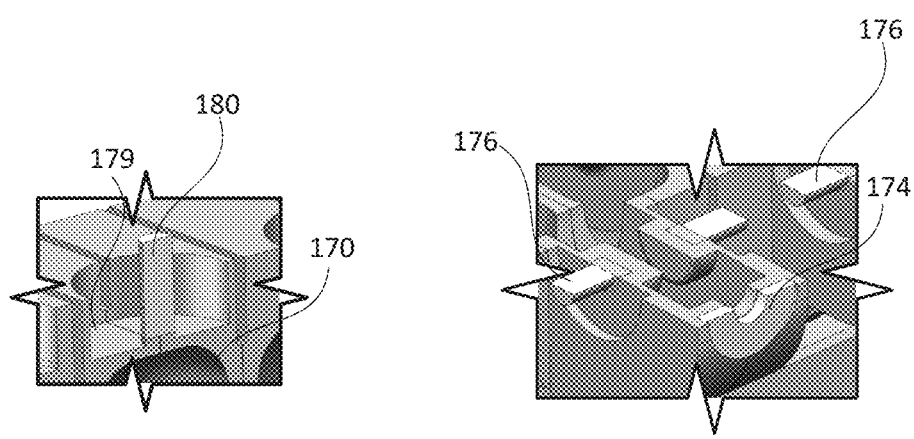
FIG. 12B
FIG. 12C

COMPACT LINEAR ACCELERATOR WITH ACCELERATING WAVEGUIDE

CROSS-REFERENCE TO RELATED APPLICATIONS

This application is a continuation of U.S. patent application Ser. No. 16/675,058, filed Nov. 5, 2019, entitled "COMPACT LINEAR ACCELERATOR WITH ACCELERATING WAVEGUIDE," which is a continuation of U.S. patent application Ser. No. 16/276,323, filed Feb. 14, 2019, entitled "COMPACT LINEAR ACCELERATOR WITH ACCELERATING WAVEGUIDE," which is a continuation of U.S. patent application Ser. No. 15/933,257, filed Mar. 22, 2018, entitled "COMPACT LINEAR ACCELERATOR WITH ACCELERATING WAVEGUIDE," which claims the benefit of U.S. Provisional Application Ser. No. 62/476,630, filed Mar. 24, 2017, entitled "COMPACT LINEAR ACCELERATOR WITH ACCELERATING WAVEGUIDE," all of which are incorporated by reference herein in their entirety and for all purposes.

BACKGROUND

Field

The present disclosure relates to radiation therapy, in particular to beam generation and beam hardware.

DESCRIPTION OF THE RELATED ART

Modern radiation therapy techniques tend to rely on bulky machinery with a limited scope of volumetric angles at which therapy can be administered.

Systems and methods disclosed herein address various challenges related to photon therapy and photon generation.

SUMMARY

Described herein include embodiments related to linear accelerators ("linacs") and related components. A linac is a device commonly used for external beam radiation treatments for patients with diseases, such as cancer. Some linear accelerators may be used to treat a broad range of angles (e.g., solid angles) around a patient, which may include all body parts and/or organs of the patient. The linac can be configured to deliver high-energy (e.g., 6 MV) radiation (e.g., x-rays) to the region of the patient's body, such as tumors.

A linac head may include a compact accelerating waveguide. The system may also include other hardware components (e.g., magnetron, cooling, waveguide isolators, waveguide plenums, sensors). The linac head may be configured to move in a broad range of solid angles (e.g., a near-complete spherical outline) around a standard patient bed (e.g., couch). As will become clear from the following disclosure, producing an effective compact waveguide and linac head can present a variety of technical challenges, which may be solved by many of the novel design features disclosed herein.

The accelerating waveguide can be housed in a small volume. For example, the isolator may be disposed in a parallel configuration with the accelerating waveguide. As a further example, the magnetron may be perpendicular to the isolator and/or the accelerating waveguide. The linac may be fit into a compact housing. The compact configuration of the linac may increase clinical efficiency by allowing the device (with the assistance of a mechanical (e.g., robotic) arm) to be maneuvered with six or more degrees of freedom inside of a treatment room. The radiation device may be compact enough to treat a patient across a large range of angles in order to maximize the dose to the target treatment volume (e.g. tumor) while minimizing the dose to healthy issues by dynamically positioning the device relative to the patient. The housing of the various components of the radiation device may allow the mechanical arm to provide treatment to areas that were previously unreachable and/or tailor a dose profile to conform as much as possible to the tumor volume. The software that develops the treatment plan that specifies the angles and positions to deliver radiation from, as well as the shape of the radiation as manipulated by dynamic Multileaf collimators, can be programmed to minimize impact to healthy and/or radiation sensitive tissues. Increasing dose conformity can allow boosting the dose to the treatment volume, allowing higher probability of tumor control.

Some embodiments of linac systems can minimize the size of an accelerating waveguide that is capable of achieving the energy and dose output required for radiation therapy. This may be accomplished by using multiple waveguide cells that are organized linearly. In order to reduce the size, the system may include one or more side cells for coupling RF power between the adjacent accelerating cells. In some designs, one or more cells have a side tuner configured to allow tuning of each of the one or more cells so that the waveguide can provide increased RF power and hence increased electron acceleration. In some embodiments, this tuning may be available only once shortly after manufacture of the various components of the system (e.g., parts of the waveguide).

Since the power is high in a smaller space, a novel cooling system may be integrated into the waveguide.

The power of the electrons and/or microwaves that the linac generates can be high. In some embodiments, the apertures within the accelerating waveguide are small. Because the waveguide is relatively short and/or because of the size of the waveguide apertures, novel vacuum ports can be included that can provide relatively high vacuum. Two vacuum ports (e.g., one on each end of the waveguide) may be included to improve vacuum pumping.

The design of the various components of a linac head may be arranged in a way that reduces the overall size of the linac head. Accordingly, a more compact standing waveguide can be installed in the linac. The compact size and/or light weight of the linac can allow a mechanical arm to move the linac head around a patient in a treatment bed and/or within a treatment room through a range of angles comprising up to 360-degrees about a first axis defined by the intersection of the x- and y-planes as well as 360-degrees about an orthogonal axis. Previous linac machines have unusable and/or unreachable angles of therapy delivery. Moreover, the waveguide cells can be manufactured to optimize the power that is available from a combination of microwave generator (e.g., magnetron) and/or electron generator (e.g., electron gun) using specific sizes, shapes, and/or tunings.

BRIEF DESCRIPTION OF THE DRAWINGS

Certain embodiments of the present disclosure will now be described, by way of example only, with reference to the accompanying drawings. From figure to figure, the same or similar reference numerals are used to designate similar components of an illustrated embodiment.

FIG. 5A is a cutaway perspective drawing of an electron gun vacuum flange.

FIG. 5B is a cutaway perspective view of the electron gun vacuum flange of FIG. 5A installed within a linac head.

FIGS. 12A-12C illustrate an example standing waveguide with cell tuning components.

DETAILED DESCRIPTION

Various systems and individual components, as well as associated methods, are disclosed herein. In some embodiments, a system is composed of four main modules: a linac head, which may contain a radio frequency (RF) power source and a linac waveguide (e.g., standing waveguide (SWG)); an electronics rack, which may include a gun deck to power an electron gun, a modulator to power a microwave generator (e.g., magnetron), and other elements; a temperature control unit (TCU), which may distribute coolant (e.g., water) in a closed-loop for power dissipation; and a control console, which may be integrated into the electronics rack and/or configured as a standalone unit to allow for placement in a remote location.

The details of the design of the various subsystems of some embodiments are included in the following sections.

Linac Head

Figure 1:
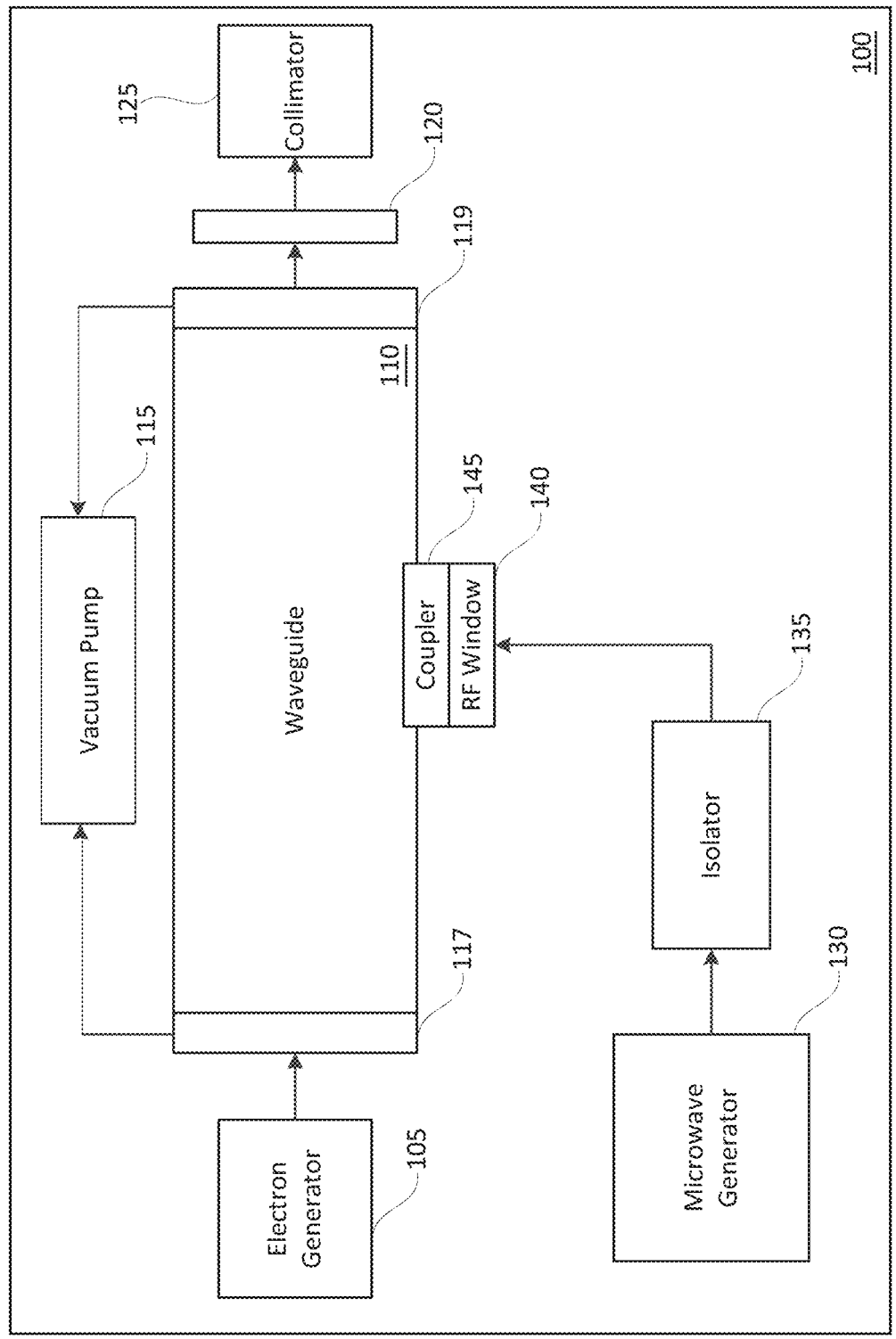
FIG. 1 is a schematic diagram illustrating components of a linac head in accordance with an exemplary embodiment.
Figure 2:
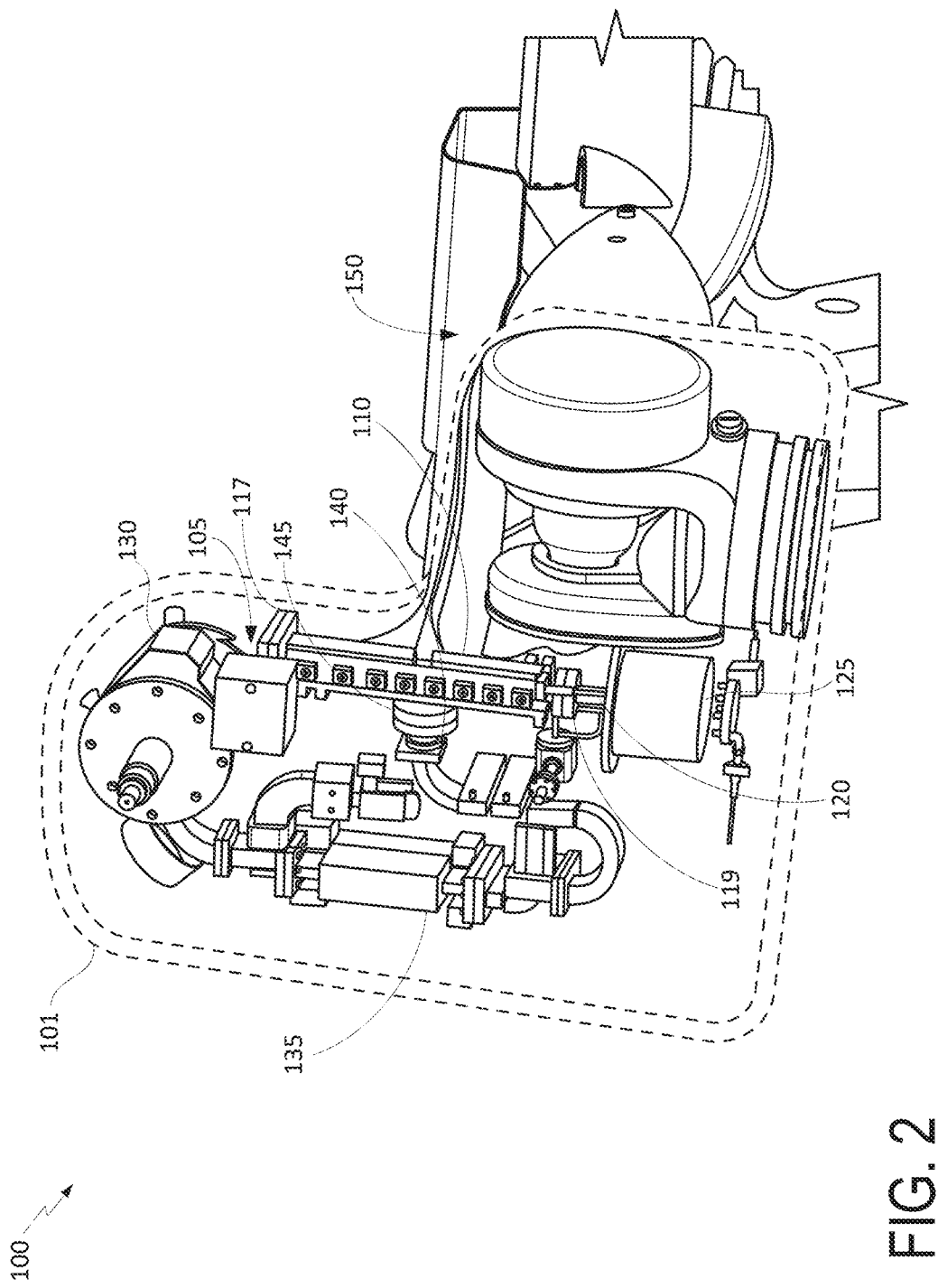
FIG. 2 is a cutaway perspective drawing of the linac head of FIG. 1.

FIGS. 1 and 2 depict example compact linac heads and components thereof. FIG. 1 schematically illustrates the various components of the linac head 100. FIG. 2 is a cutaway perspective drawing illustrating example elements as installed in the linac head 100 and/or system. Some designs use a linear accelerating structure (e.g., accelerating waveguide 110) using microwaves at one or more ranges of frequency (e.g., X band, S band), which may be between about 7.0 and 11.2 GHz, such as, for example, at approximately 9300 MHz, to accelerate electrons at one or more ranges of kinetic energy (e.g., between about 2 MeV and 8 MeV). Other designs can be used to accelerate electrons having higher or lower energies. In some embodiments, a photon (e.g., x-ray) beam with a dose rate between about 300 cGy/min and 1,800 cGy/min (e.g., approximately 1,000 cGy/min) can be generated at about 1 m from the X-ray converter.

Referring jointly to FIGS. 1 and 2, an example embodiment of a linear accelerator head 100 for use in a radiation therapy system can include a housing 101, an electron generator 105, a waveguide 110 configured to contain a standing or travelling microwave, the waveguide comprising a plurality of cells disposed adjacent to one another, wherein each of the plurality of cells comprises an aperture configured to allow electrons to pass therethrough, a converter 120 disposed along a beam path of the electrons and configured to convert electrons to photons, and a primary collimator 125 configured to shape the resulting X-ray beam.

The linac head 100 further includes a vacuum pump 115 for removing particles, gases, and the like, from the waveguide 110 through an electron gun vacuum flange 117 and a converter vacuum flange 119. A microwave generator 130 produces microwave-range radiation, which can be coupled into the waveguide 110 through a RF window 140 and coupler 145. An isolator 135 transmits the RF power received from the microwave generator 130 to the RF window 140 while preventing RF power from being transmitted in the opposite direction, back to the microwave generator. As shown in FIG. 2, the compact linac head may be mounted on a mechanical arm 150. The various components described above and depicted in FIGS. 1 and 2 will be described in greater detail below.

Microwave Generator

As shown in FIG. 2, a microwave generator produces a microwave signal that may be coupled into the waveguide at a coupler 145. A microwave generation assembly may include a microwave generator (e.g., magnetron or the like). In some embodiments, the microwave generator can be an oscillator that converts DC pulses from a modulator into RF power. As described above, the microwave generator may produce a power greater than 1.5 MW. The microwave generator may include a tuning mechanism to adjust an output frequency. In some designs, the tuning mechanism may allow the output frequency to be tuned from between about 9.27 GHz to 9.33 GHz. The microwave generator may include a water-cooled anode and/or focusing magnet. A filament of the microwave generator may be configured to supply over 2,000 hours of operation. The microwave generator may further include an ion pump. In some embodiments, the ion pump can produce about 0.4 l/s.

Isolator

An isolator may be included in the microwave generation assembly. The isolator can be configured to prevent microwaves from traveling back into the microwave generator. The isolator may have two or more loads attached to it (e.g., it may have 4 ports on it). For example, it may include a main pass and/or two auxiliary ports.

RF Window

The microwave generation assembly may include an RF window. An RF window may be configured to separate gas inside the microwave generation assembly from entering the waveguide, which may be under vacuum. As shown in FIG. 2, the RF window may be disposed proximate the waveguide and/or attached directly to the coupler. The RF window may include cooling to prevent overheating. The position of the RF window is also selected to place it at a minimum of the reflected standing wave field such that the heating is minimized.

Coupler

A coupler (e.g., coupler cell) may be included as part of the waveguide. The coupler may receive microwaves from the microwave generation assembly and propagate the waves into and/or through the waveguide.

Mechanical Arm

A mechanical (e.g., robotic) arm may be included in a radiotherapy system. The mechanical arm may provide support and/or movement for the linac head. Using the mechanical arm, the linac head may be able to reach large ranges of angles of radiation therapy delivery.

Electron Gun

The electron generator 105 (e.g., electron gun, electron emitter) may produce electrons along a range of angles. In some embodiments, the electron generator 105 produces a collimated electron beam. The electron beam may be configured to produce a range of kinetic energies. Electron generators may be classified by the type of electric field generation (DC or RF), by emission mechanism (thermionic, photocathode, cold emission, plasmas source), by focusing (pure electrostatic or with magnetic fields), or by the number of electrodes.

Figure 3:
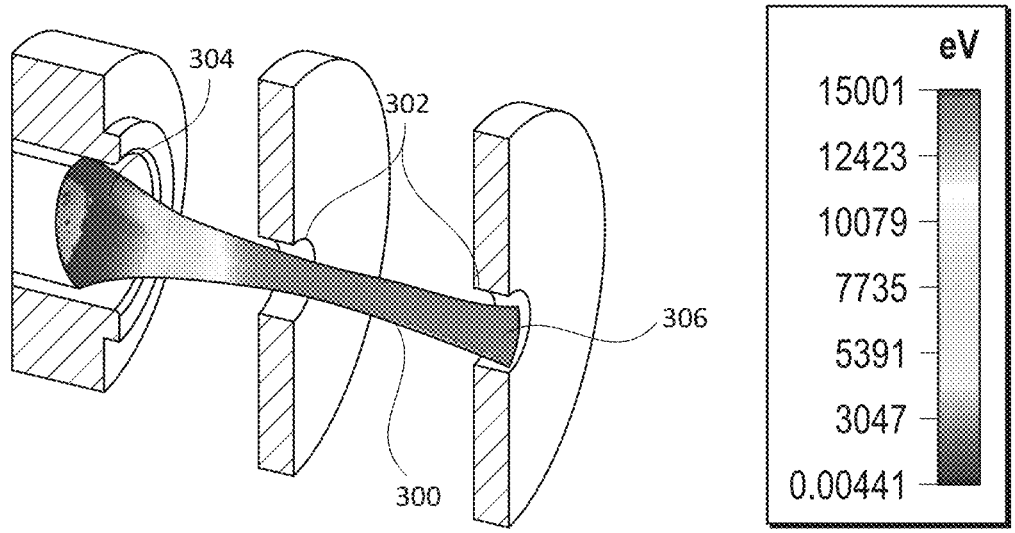
FIG. 3 illustrates an energy level range of electrons passing through a waveguide aperture.
Figure 4:
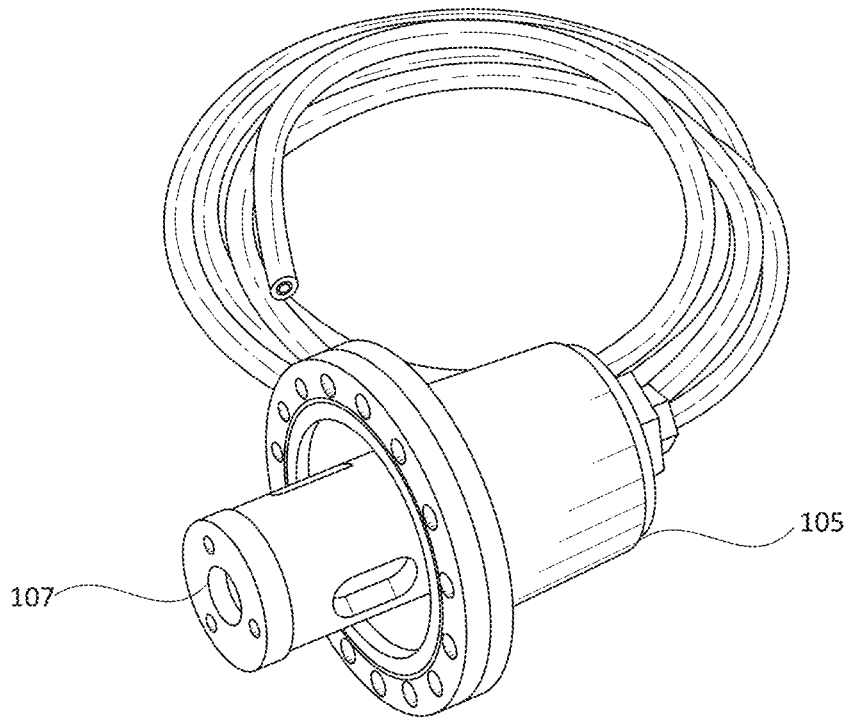
FIG. 4 illustrates an example coupling of components of an example linac head.

FIG. 3 illustrates an energy level range of some electrons produced by electron generator 105 passing through waveguide apertures 302. As shown in FIG. 3, the beam 300 begins at 304 as a relatively low-energy beam, accelerating to a higher energy level at 306 traveling through the waveguide. FIG. 4 illustrates an example coupling of two parts of one embodiments of a linear accelerator head. A linear accelerator head may use an electron generator 105, such as an L-3 M592 or other model. A cathode may be separated from an anode by a distance of between about 4 mm and 22 mm (e.g., about 10 mm). The electron gun may provide, for example, a 15 keV DC beam that can be focused into an aperture of the accelerating section (e.g., waveguide) of the linac head, for example, at output aperture 107. The aperture may have a diameter of between about 1 mm and 15 mm (e.g., about 2 mm). The emitted current is adjusted by the proper choice of grid voltage in the range of about −65 V (0 A) to 70V (1.4 A). Other ranges are also possible. The performance of some embodiments of the electron gun and the beam quality can be verified with beam dynamics simulations, using codes such as EGUN, CST Particle, and PARMELA.

Electron Gun Vacuum Flange

An electron gun vacuum flange 117 can be configured improve vacuum conductance in the beginning of the waveguide 110 (e.g., standing waveguide or SWG). An electron gun vacuum flange 117 (e.g., electron gun vacuum flange) may be oriented so that it can generate fluid flow from an interior of the electron gun chamber and/or the waveguide 110. In some designs, the waveguide 110 is comprised of cells that include an aperture having a diameter of less than about 1 cm. Due to fluid dynamic restrictions on fluence for apertures smaller than about 1 cm, the electron gun vacuum flange can provide fluid communication between a vacuum pump and the interior of the electron gun chamber and/or the waveguide 110. In some embodiments, the aperture is about 4 mm in diameter. The diameter may be between about 1 mm and 7 mm.

The electron gun vacuum flange 117 may be disposed between electron generator and the waveguide. Accordingly, the electron gun vacuum flange 117 includes a waveguide coupling section 152, a waist 154, and a vacuum pump coupling section 156. An aperture 158 is in fluid communication with the interior of the waveguide 110 and the vacuum pump coupling section 156, such that a vacuum pump coupled to the vacuum pump coupling section 156 (e.g., directly or by an intermediate conduit) can effectively remove gases or particles from the interior of the waveguide 110 at the electron gun end of the waveguide 110. In some embodiments, the electron gun vacuum flange 117 includes an aperture 111 that is coaxial with a beam axis along a beam of electrons. In some embodiments, the electron gun vacuum flange 117 defines one or more channels configured to pass fluid therethrough.

Waveguide

The waveguide 110 (e.g., standing waveguide or SWG) may be made of copper and may have a length of between about 20 cm and 75 cm. In some designs, the waveguide is about 30 cm long. The waveguide may be able to accelerate electrons having an initial energy of about 10 keV to about 6 MeV at the output of the waveguide.

Figure 6:
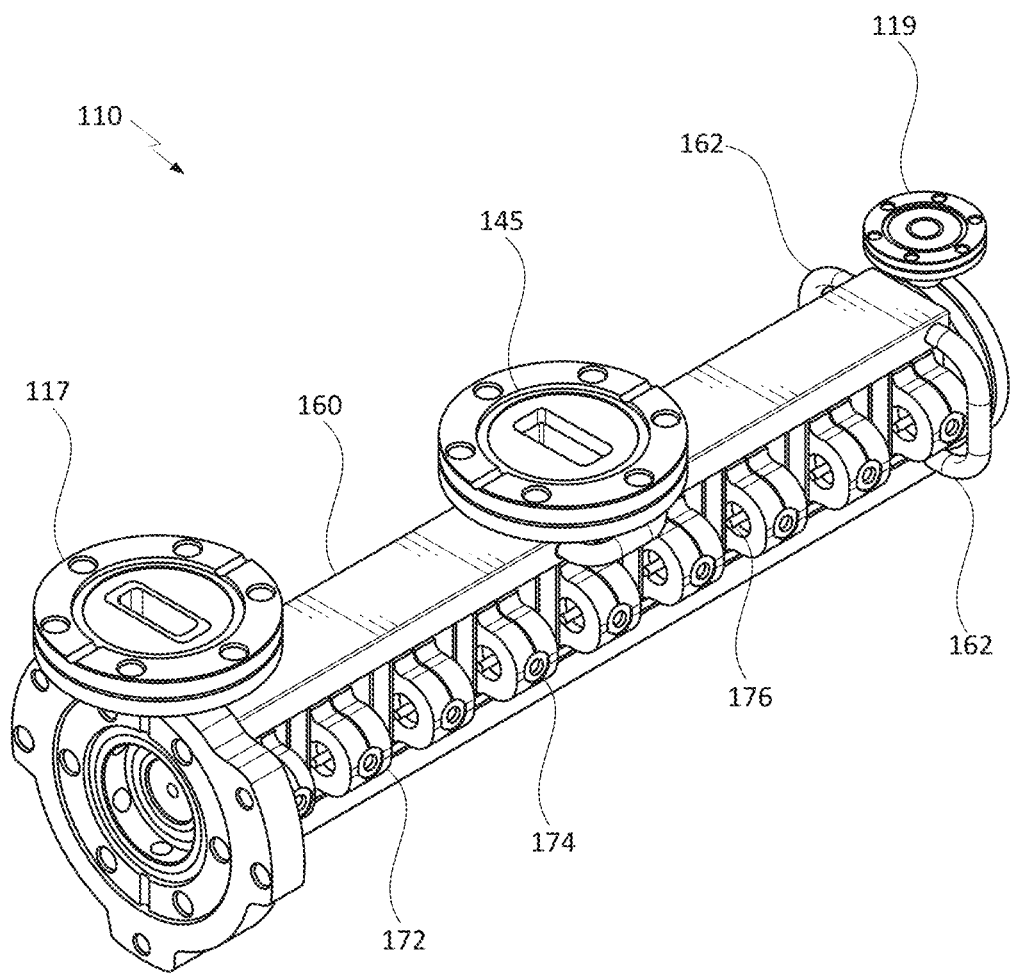
FIG. 6 illustrates an example standing waveguide.

FIG. 6 illustrates an example standing waveguide 110 in accordance with the linac head embodiments disclosed herein. In some embodiments, the waveguide 110 includes one or more coupling cells 172 (e.g., side cells, sub-cells, etc.). The coupling cells 172 may be disposed on one or another side of the waveguide 110 (e.g., opposite sides) and may be offset from corresponding coupling cells on an opposite side of the waveguide 110 by an offset distance. The offset distance may be tuned to allow a standing wave to oscillate within the waveguide 110. The waveguide can be configured to achieve one or more modes (e.g., resonant frequencies), such as, for example, $\pi$ or $\pi/2$. Bi-directional tuners 176 may be included on the side cells. One or more cooling blocks 160 may be disposed on the top and/or the bottom of the standing waveguide 110 which prevents the waveguide from overheating and keeps the frequency of the accelerating mode within the range of tunability of the RF power source. Since the waveguide 110 may be smaller than traditional waveguides used in medical radiotherapy, a relatively large surface area of the one or more cooling blocks 160 can be in thermal communication with the waveguide 110. The cooling block(s) 160 may provide temperature control for the waveguide 110. In some embodiments, the cooling blocks 160 may include additional holes, grooves and/or slots, for example, to provide access to a user to one or more elements of the waveguide 110 (e.g., tuners, shorting openings). Such grooves and/or slots may provide access to certain portions of one or more cells of the waveguide 110, for example, to tune them (e.g., through the tuning pins). In some embodiments, tuning may be performed after the one or more cooling blocks 160 have been attached. Coolant conduits 162 in communication with interior volumes of the cooling blocks 160 allow a common quantity of coolant to flow through the cooling blocks 160, although the cooling blocks 160 may be separately cooled in some embodiments.

Without being limited by theory, it is believed that reducing the length of the waveguide can require smaller apertures within the accelerating cells of the waveguide. Smaller apertures can further reduce fluence (e.g., for a vacuum)

through the waveguide. Therefore, for waveguides of certain dimensions, if one large pump is used, there may be insufficient vacuum conductance in parts of the waveguide (e.g., near the electron generator and/or near the converter). Accordingly, two or more vacuum ports/flanges may be used through which vacuum generation within the waveguide may be achieved. For example, an electron gun vacuum flange 117 may be included near the electron generator (e.g., between the electron generator and the waveguide), a converter vacuum flange 119 may be included near the converter (e.g., between the waveguide and the converter) (see, e.g., FIGS. 21-22), and/or a coupler 145 may be included to allow vacuum generation through one or more of the cells of the waveguide 110 (e.g., through a coupling cell).

Operation of the system (e.g., at the cathode of the electron beam) may produce heat that can raise the temperature of the material of the cells (e.g., copper). The heat may also allow gases to be liberated from materials in the system. This may increase the vacuum pressure (e.g., reduce vacuum). This heat may be produced, for example, by the electron gun and/or by the converter. The electron gun may include a cathode that may be heated by a filament to raise a temperature of the cathode to raise the energy electrons within the cathode above the work function of the cathode, in order to extract them for propagation through the waveguide. At the converter, electrons may be incident on a disc (e.g., a foil). The disc may comprise one or more materials, such as, for example, tungsten, lead, aluminum, copper, an alloy comprising metal elements, etc. When electrons are incident upon the disc, heat is produced. It may be advantageous to draw the heat produced away from the converter, which may be done by including cooling channels within or around the converter.

A relatively short waveguide 110 may promote higher electric fields therein. The higher electric fields may require high or ultrahigh vacuum levels, with pressure of $10^{-7}$ Torr or lower, in order to avoid breakdown of the electric field on the surface of the waveguide. Combined with a smaller aperture within the waveguide 110, it can be advantageous to evacuate the waveguide 110 and/or other components of the system. Accordingly, the vacuum flanges 117, 119 may be installed at one or more ends of the waveguide. This may provide a desired vacuum conductance at certain portions of the system, (e.g., one or more ends of the waveguide 110).

Tuning features may be included in the system. In some embodiments, tuning features are included in one or more cells of the waveguide, such as the accelerating cells (e.g., bunching cell(s), coupler cell(s), standard cell(s)) and/or side cells (e.g., coupling cells). The tuning features may provide, for example, the side cells with a correct frequency of microwave. In some designs, the accelerating cells may be more precisely tuned. The tuning features may provide structures configured to allow a user to tune one or more of the waveguide cells.

A tuning process may include tuning one or more of the side coupling cells 172. The side cells may be tuned separately. This may be accomplished by using an antenna assembly to indicate to what extent the cell should be tuned. Accordingly, the side cell may be tuned to the correct frequency. In some implementations, an object such as a shorting pin may be inserted into one or more of the side coupling cells. A shorting pin may be inserted through openings 174 in the side of the one or more side coupling cells 172. Insertion of the shorting pin may allow the side coupling cells 172 to be electrically shorted. In may be advantageous to electrically short one or more of the side coupling cells 172 during tuning of one or more of the accelerating cells. For example, shorting one or more of the side coupling cells 172 may allow for more accurate measurements to be received from only the accelerating cells. Tuning one or more of the accelerating cells may be performed by looking at the "field balance," a measurement of the longitudinal electric field amplitude along the length of the waveguide 110. An antenna assembly and/or a "bead pull" system may be used for tuning the one or more accelerating cells. This may be done while one or more side coupling cells 172 are shorted.

Figure 7:
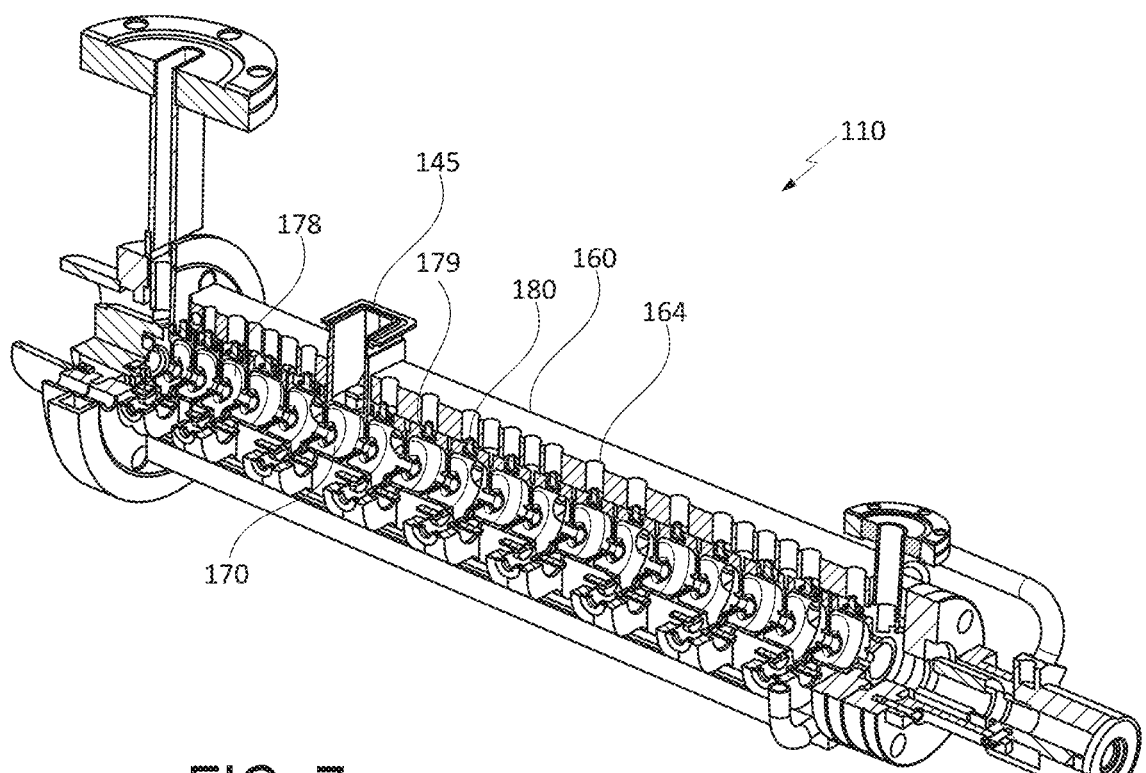
FIG. 7 is a cutaway perspective view of an example standing waveguide.

FIG. 7 is a cutaway view illustrating an example waveguide 110. The waveguide may contain fewer than 24 accelerating cells 170. In some designs, the waveguide contains 19 cells. The cells may be machined out of metal (e.g., copper, a copper alloy). The length of the waveguide 110 may be less than about 70 cm. In some embodiments, the waveguide has a length of about 30 cm. The waveguide 110 may include shorter bunching cells 178 in addition to standard accelerating cells 170.

The accelerating cells 170 may also be configured to be bi-directionally tuned using, for example, tuning studs 180. The tuning studs are depicted and described in greater detail below with reference to FIGS. 6, 7, 12B, 12C and 14. Two or more tuning studs 180 may be included on a cell. As described above, the cooling block 160 includes openings 164 to permit access to the tuning studs 180. Including a plurality of tuning studs 180 may allow for a greater range of frequency to be tuned, or finer tuning and/or accuracy in tuning. In some embodiments, the tuning studs 180 allow a user to attach a tuning attachment that is configured to allow the user to deform the cell (e.g., accelerating cell 170, side cell). The deformation of the cell may be accomplished using, for example, a slide hammer or other implement. The tuning studs 180 (FIG. 7), 176 (FIG. 6) may be threaded to facilitate coupling of the slide hammer or other tuning implement. In some embodiments, the one or more cells are configured to be tuned once before use of the system. Other implementations are possible.

The accelerating cell tuning studs 180 may be brazed along a top and/or bottom of the waveguide 110. For example, the tuning studs 180 may be brazed into pockets 179 located along the waveguide 110. This may be done at an equator of one or more of the cells. In some embodiments, the pockets 179 may be created after assembly of the waveguide 110 (e.g., after the accelerating cells 170 are coupled together), and prior to brazing the accelerating cell tuning studs 180. For example, a manufacturing process may include assembling the accelerating cells 170 and the cooling block 160 (which may already contain openings 164), such as by brazing, followed by machining the pockets 179, then brazing the tuning studs 180 within the machined pockets 179. Other manufacturing processes are possible. One or more of the side cell studs 176 (FIG. 6) may be brazed along the axes of the side cells. In some embodiments, the pumping flange and converter flange may be welded (e.g., tungsten inert gas (TIG) welded, electron beam welded, etc.) to the waveguide 110 after it is tuned. As described above, one or more side cells may include an opening for insertion of shorting pins for tuning purposes. After tuning, the opening in the one or more cells may be sealed (e.g., hermetically) with a plug. The plug may be welded to cover the opening.

Figure 8:
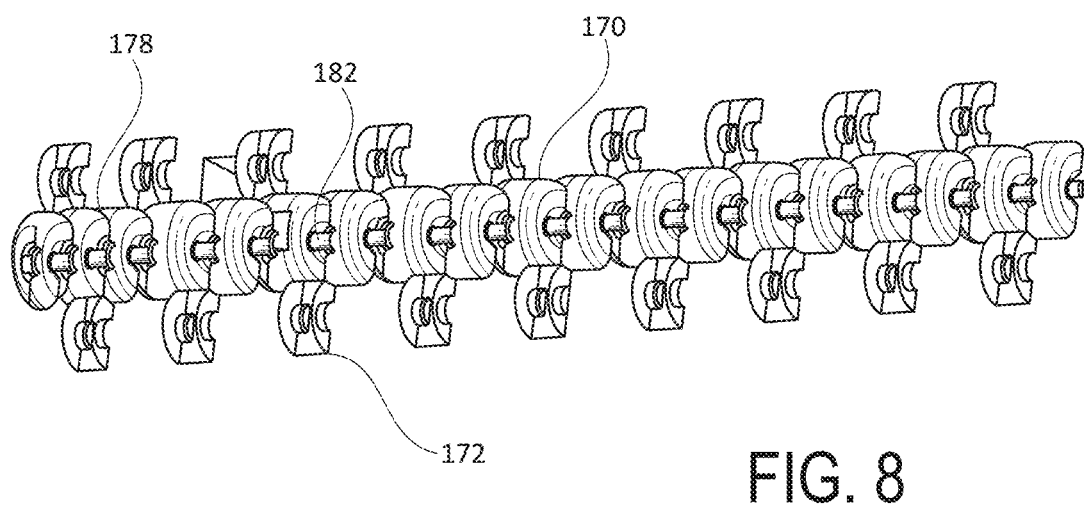
FIG. 8 illustrates an example internal geometry of a standing waveguide.

In some embodiments, one or more cells of the waveguide 110 are brazed to one or more vacuum flanges (e.g., electron gun flange, converter flange). The vacuum flange may include a conflat flange. A side coupled structure comprising one or more side cells may be used to achieve π/2 standing wave mode. FIG. 8 shows an example geometry of a waveguide. The microwave generator may produce a power greater than 1 MW. In some implementations, the microwave generator can produce a power of about 2 MW. The microwave generator may produce microwaves at a frequency of between about 7.0 and 11.2 GHz. In some designs, the microwave generator generates microwaves at about 9.3 GHz.

Figure 9:
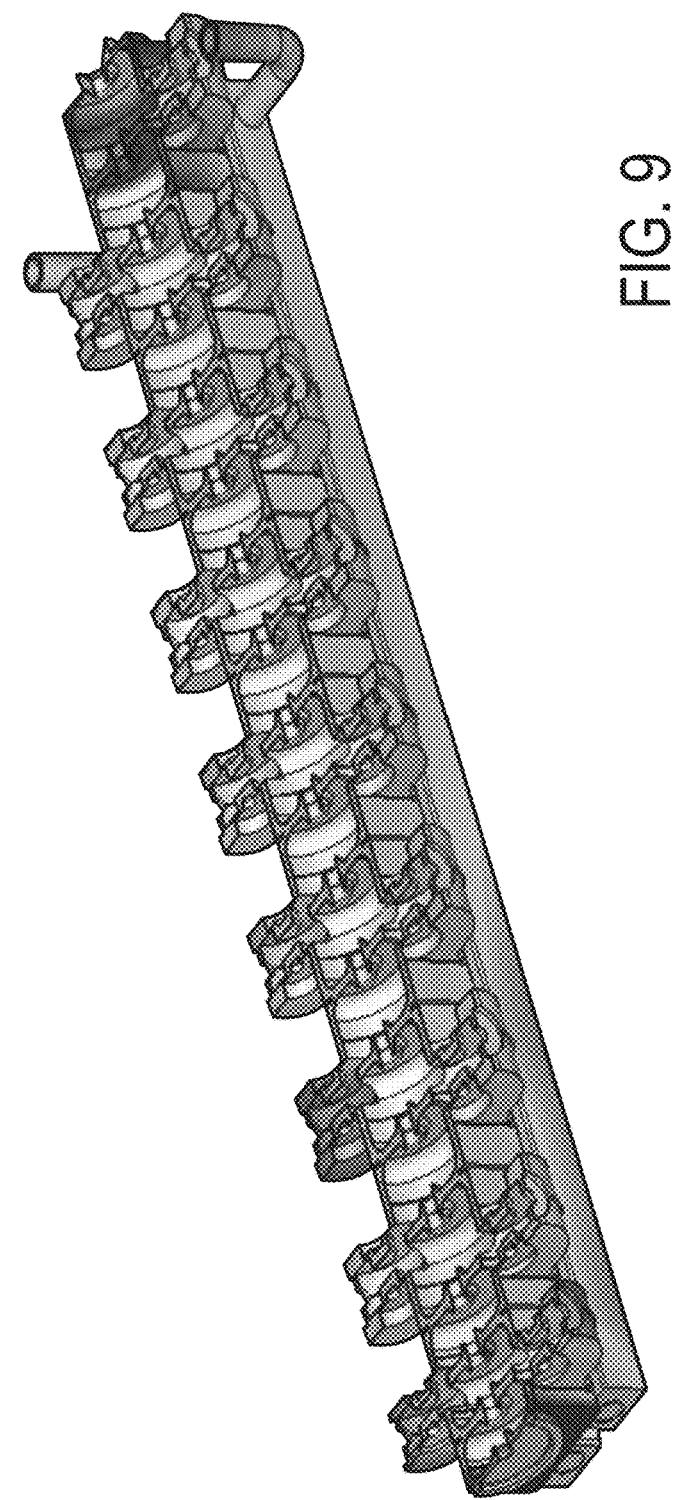
FIG. 9 illustrates the effects of heating on the geometry of a standing waveguide.

A structural analysis may be performed on various parts of the system to estimate the adverse effects of heating of various components of a waveguide. FIG. 9 shows an example of a structural analysis of a waveguide, illustrating thermal expansion of various portions of the waveguide due to heating.

Figure 10:
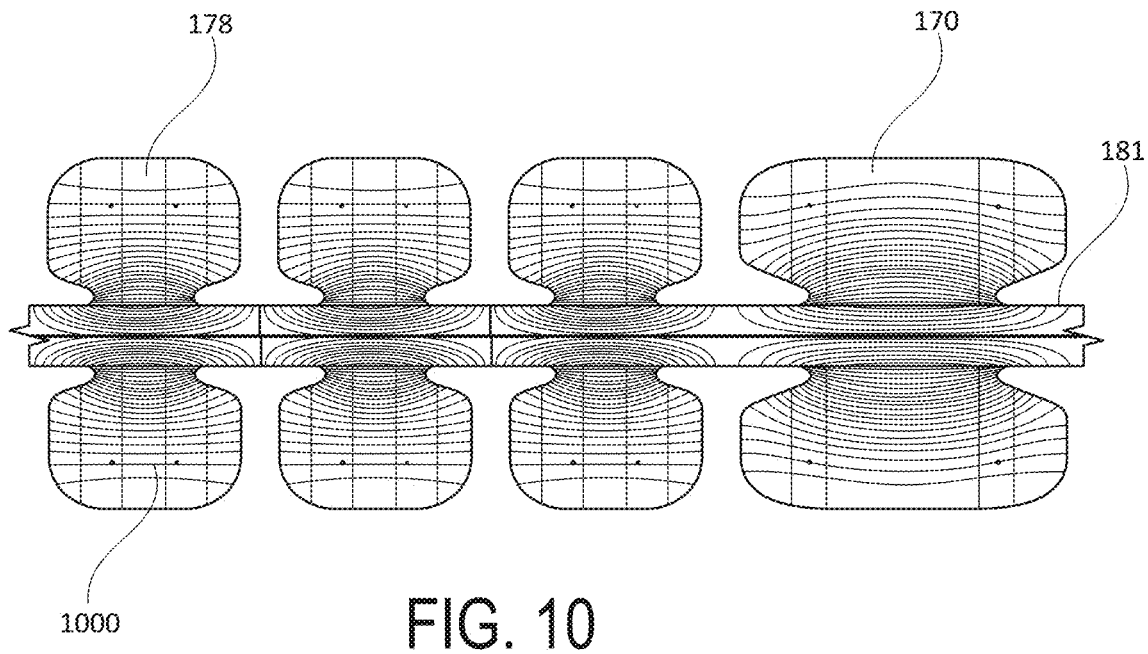
FIG. 10 is a cross-sectional view illustrating the electric field distribution in an example group of bunching cells and an accelerating cell.
Figure 11:
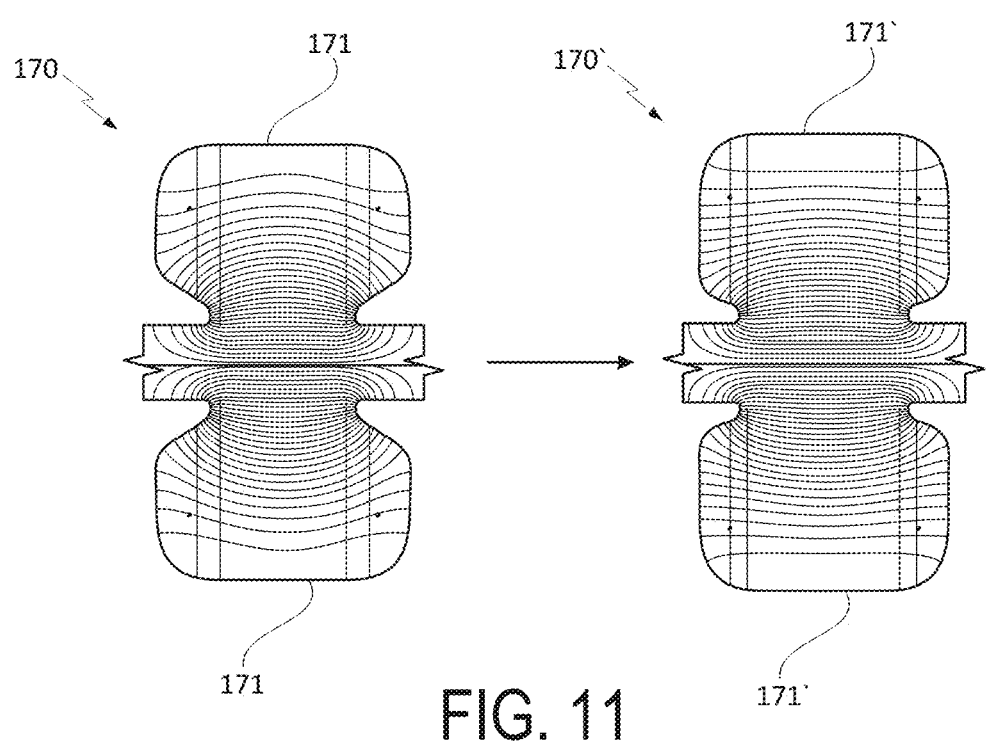
FIG. 11 is a cross-sectional view illustrating the effect on electric field distribution of tuning a waveguide by altering the shape of a cell.

Referring now to FIGS. 10 and 11, in order to accelerate the electrons from the energy provided by the electron gun, e.g., about 15 keV, to an energy at which the electrons are traveling at highly relativistic velocities, e.g., about 1 MeV, one or more bunching cells 178 may be provided. FIG. 10 schematically illustrates three bunching cells followed by a standard accelerating cell 170. Apertures 181 permit the flow of electrons between the cells 170, 178. The bunching cells 178 may have a shorter length (e.g., defined along a beam axis of the system) compared to standard accelerating cells 170. The bunching section may produce a transmission efficiency of about 40% for an acceleration gradient of between about 15 MV/m and 30 MV/m. The electric field distribution within the depicted portion of the waveguide is indicated by lines 1000.

FIG. 11 shows the effects of tuning. The shape of a cell (e.g., accelerating cell 170) may be altered to increase shunt impedance. As described above, the cells may be tuned using tuning studs disposed at the exterior of the waveguide. Manipulation of the tuning studs can move the cell wall 171 inward or outward. For example, the cell 170 of FIG. 11 is altered by moving the cell walls 171 outward. Cell 170' has cell walls 171' extending further from the central axis. An example of the resulting alteration of electric field distribution is shown in FIG. 11.

Figure 13A:
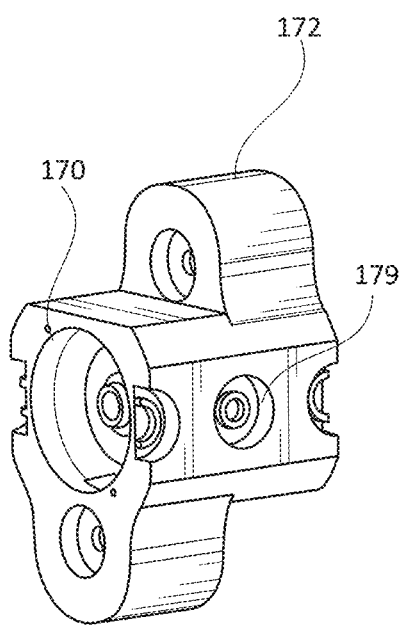
FIGS. 13A and 13B illustrate example geometries of waveguide cells including side cells.
Figure 13B:
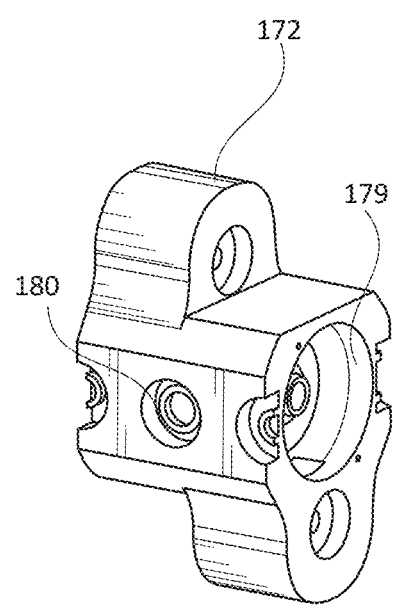
Figure 14:
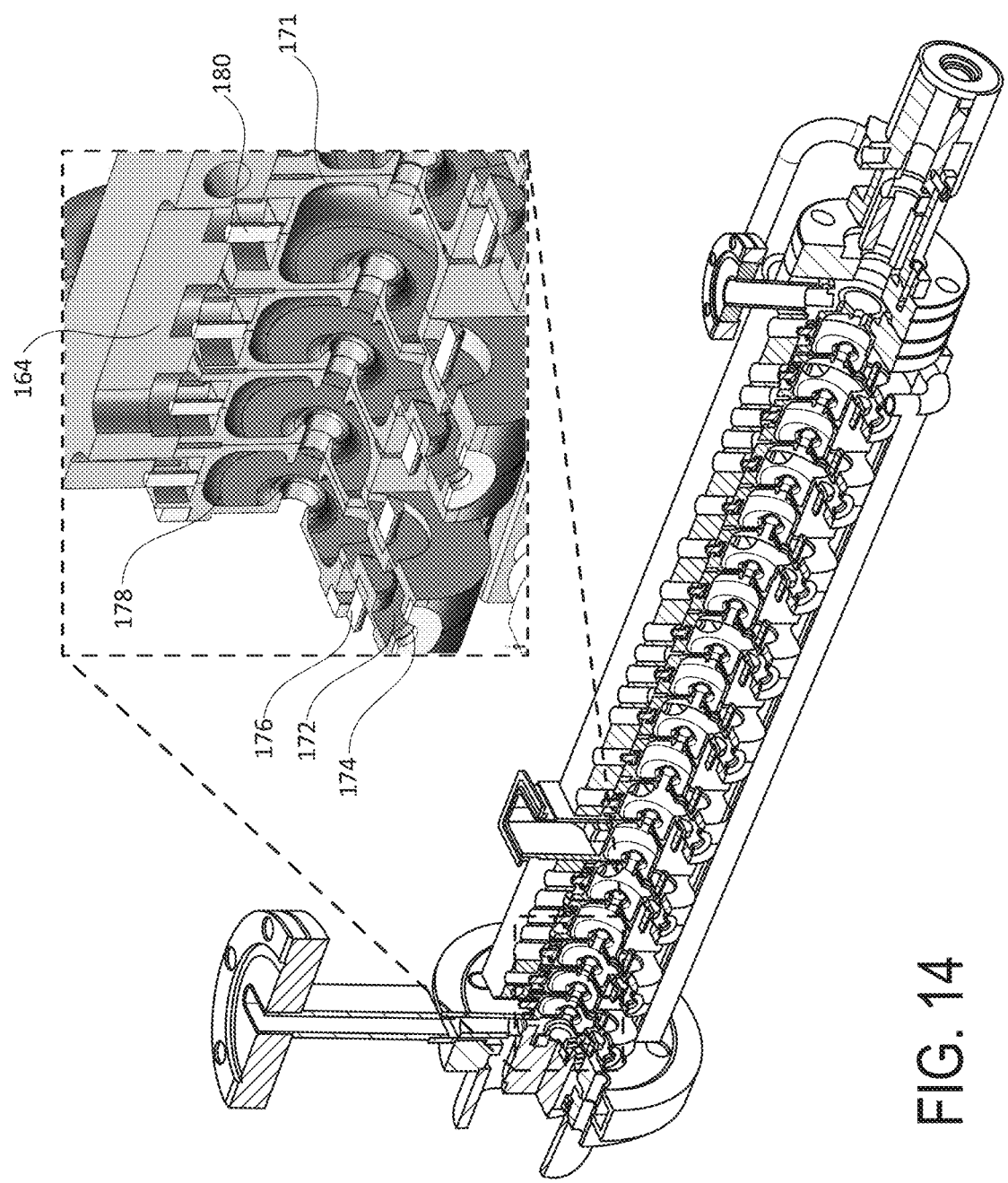
FIG. 14 illustrates tuning structures of an example linac waveguide.

FIGS. 12A-12C illustrate a waveguide with enlarged portions illustrating example tuning structures in FIGS. 12B and 12C as described above. FIGS. 13A and 13B illustrates cell geometries with accelerating cells 170, side coupling cells 172, along with some milled portions during manufacture. FIG. 14 is a cutaway view further illustrating example tuning structures (in the enlarged cutaway section of bunching cells 178, coupling cells 172, and accelerating cells 170), as described above.

Cooling System

Figure 15A:
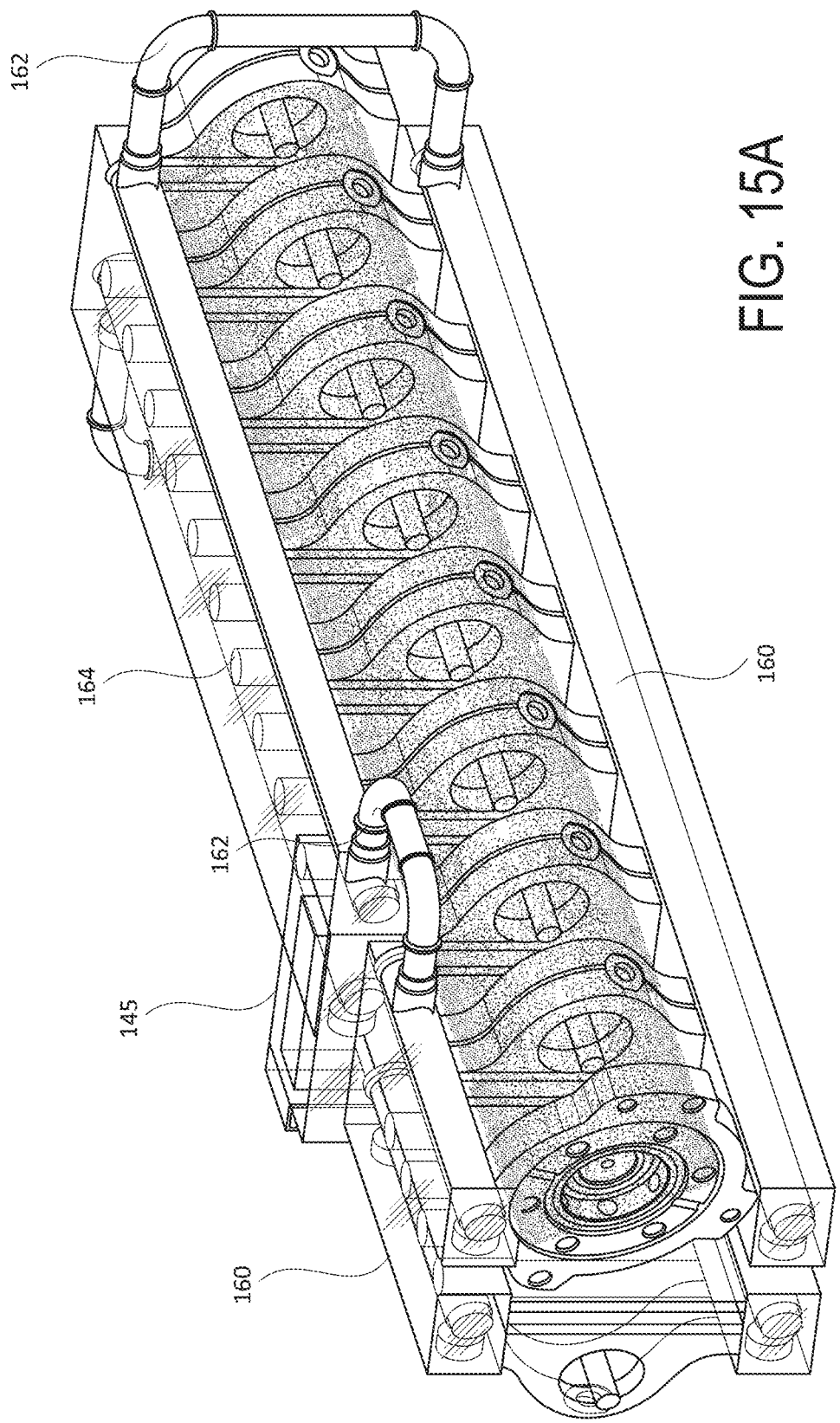
FIG. 15A illustrates an example cooling system for a linac waveguide.
Figure 15B:
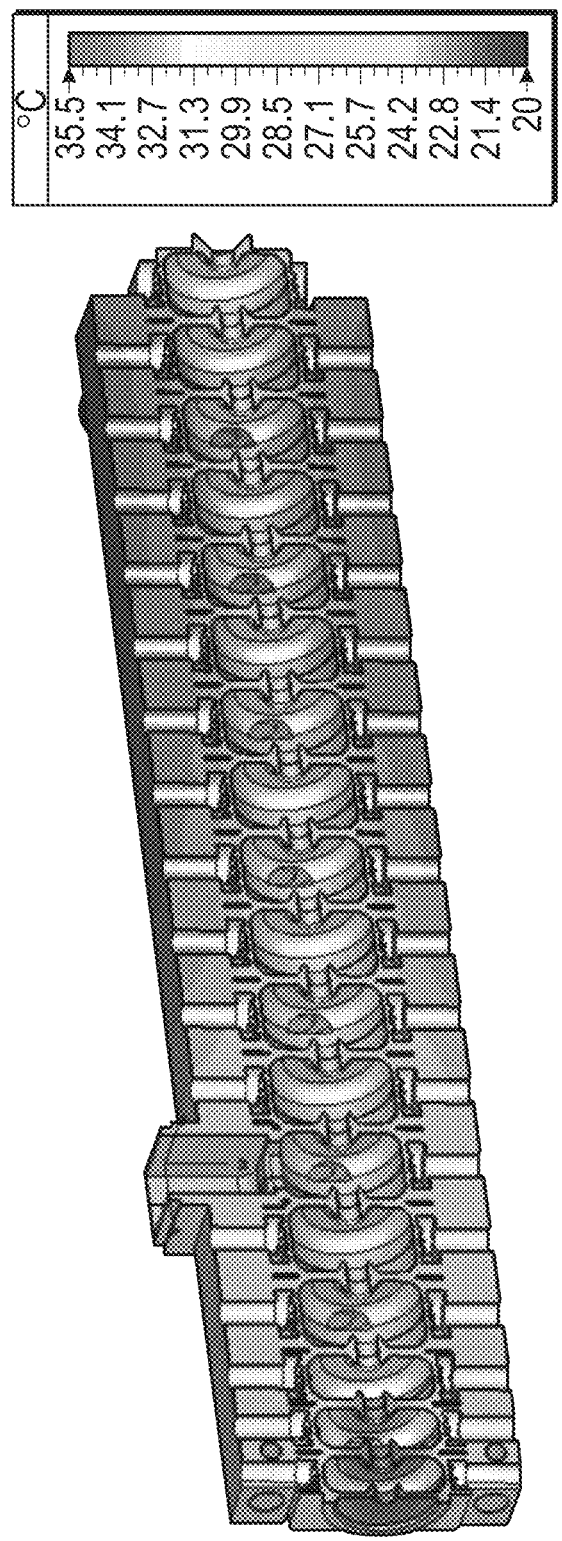
FIG. 15B depicts a temperature distribution of a linac waveguide cooled with the cooling system of FIG. 15A.

FIG. 15A illustrates an example cooling system that includes cooling blocks 160 (e.g., a cell plate) with a channel allowing fluid to flow therethrough. Conduits 162 permit a common quantity of coolant to flow between the cooling blocks 160. In some embodiments, conduits 162 may further be configured to carry coolant to and from other cooling components, for example, coolant paths for cooling additional components such as the electron generator, converter, or other components of the linac head (not shown in FIG. 15A) that may generate heat during operation and/or that may have a desired operating temperature range. FIG. 15B shows relative heat distribution in one embodiment of a waveguide with a cooling system consistent with the cooling system depicted in FIG. 15B. As shown by FIGS. 15A and 15B, the waveguide may be surrounded on opposite sides by a cooling plate. A relatively higher temperature may be produced in and/or near the bunching cells at the electron generator end of the waveguide 110 due to, for example, the higher power density present at this location.

Figure 16B:
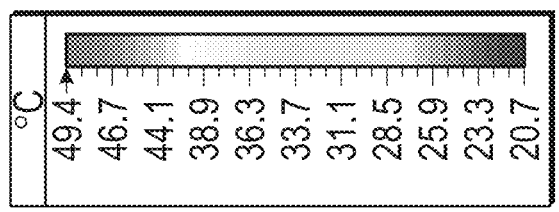
FIG. 16B depicts a temperature distribution of a linac waveguide cooled with the cooling system of FIG. 16A.
Figure 16B:
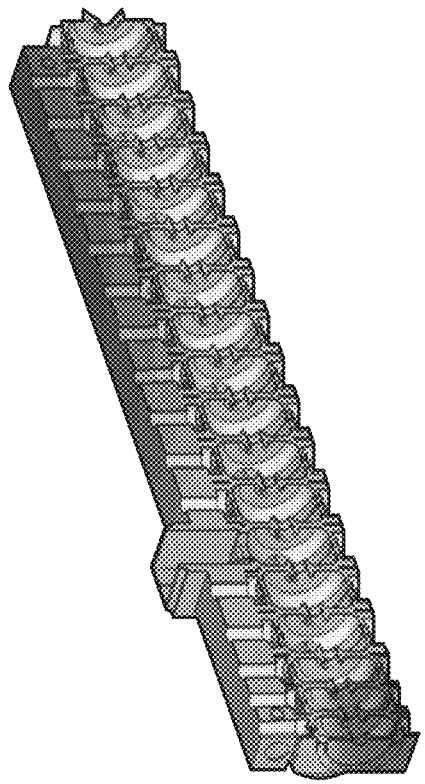
Figure 16A:
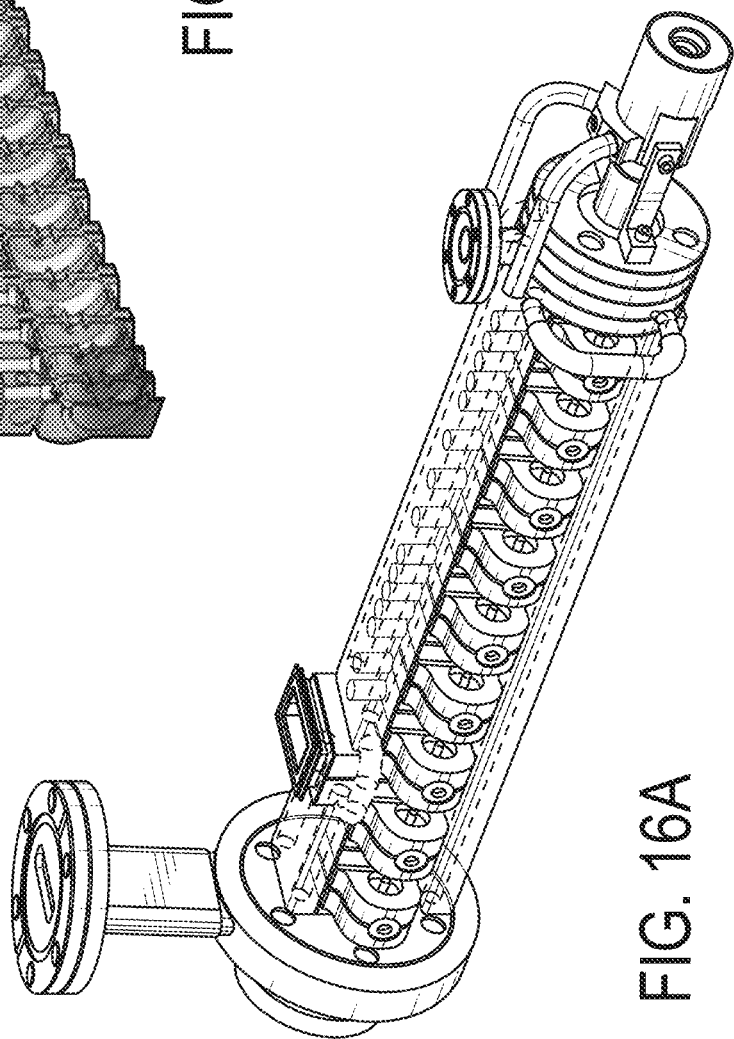
FIG. 16A depicts an alternative cooling system configuration for a linac waveguide.

FIGS. 16A and 16B illustrate a further embodiment of an example waveguide with associated heat signatures. Waveguides that propagate microwaves in the X band frequency range (e.g., between about 7.0 GHz and 11.2 GHz) may promote smaller apertures within the waveguide than, for example, microwaves in the S band frequency range. Smaller apertures within the waveguide can reduce fluence from an interior of the waveguide to a vacuum pump. As described above, use of vacuum flanges at one or both ends of the waveguide may promote a lower pressure within the waveguide by, for example, increasing fluence of gas particles out of the waveguide. This may also help improve vacuum pressure at one or both ends of the waveguide.

Converter

Figure 17:
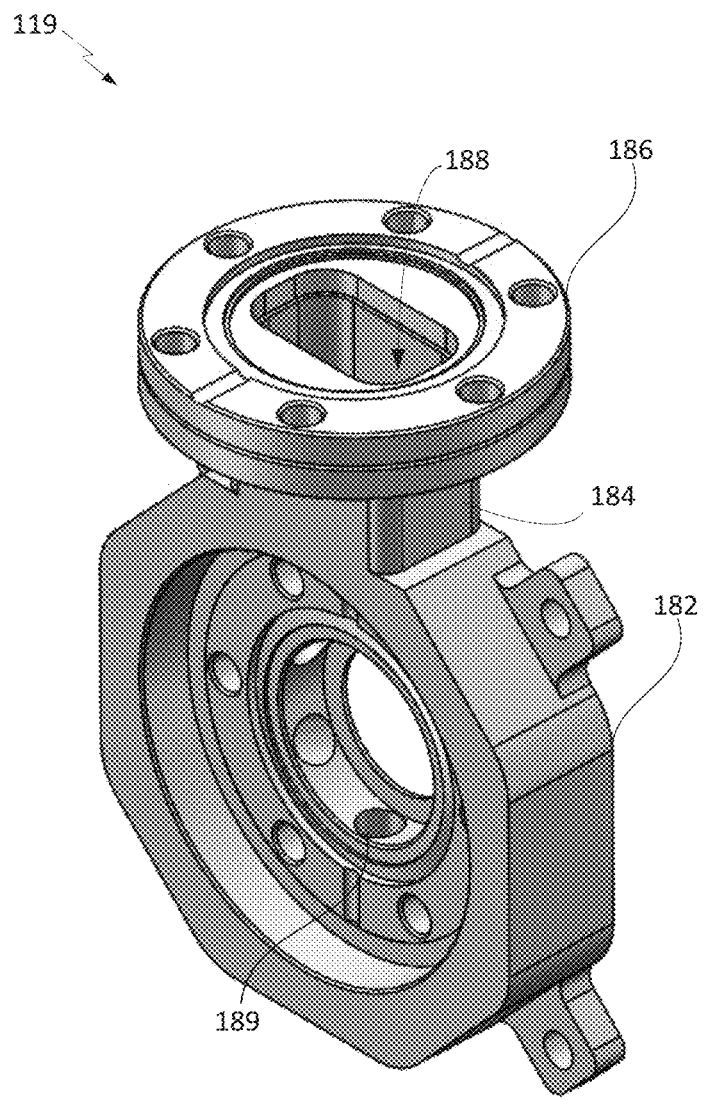
FIG. 17 is a perspective view of an example vacuum flange for a linac waveguide.
Figure 18:
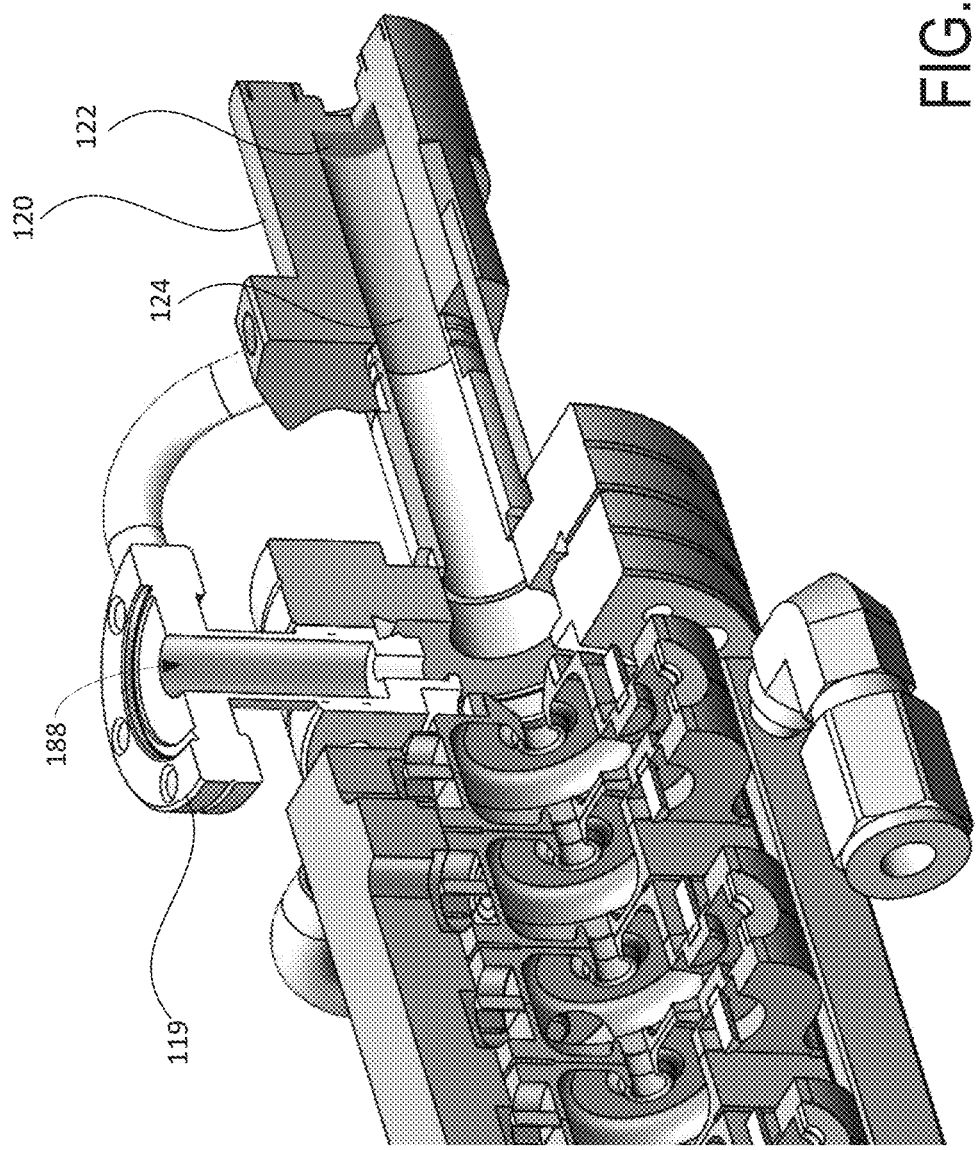
FIG. 18 is a cutaway perspective view of a converter and a converter vacuum flange installed in a linac waveguide.

As described above, and with further reference to FIGS. 17 and 18, a converter for producing photons may be provided at an end of the waveguide opposite the electron generator. FIG. 17 illustrates an example vacuum flange which may be included as the converter vacuum flange 119 configured to facilitate vacuum pumping at the converter end of the waveguide. In some embodiments, the flange depicted in FIG. 17 may also be included as the electron gun vacuum flange 117 as described above. FIG. 18 is a cutaway perspective view illustrating the converter end of the waveguide, including the converter vacuum flange 119 and converter 120 coupled thereto. The converter vacuum flange 119 generally has a similar structure and function to the electron gun vacuum flange 117 described elsewhere herein. For example, the converter vacuum flange 119 includes a waveguide coupling section 182, a waist 184, and a vacuum pump coupling section 186. An aperture 188 extends through the waist 184 and the vacuum pump coupling section 186 to provide fluid communication between the interior of the waveguide and a vacuum pump. Apertures 189 within the waveguide coupling section provide a fluid flow path between the waveguide interior and the aperture 188.

The converter is disposed at the end of the accelerating waveguide opposite the electron generator. In some embodiments, the converter 120 may be included within a collimator, or may be a standalone structure upstream from a collimator. Collimators are described in greater detail below with reference to FIG. 19. For example, the converter 120 may be between the collimator and a waveguide exit. The converter 120 may include a disc 122 (e.g., a metallic foil) disposed within an interior space 124 of the converter 120. In some embodiments, the converter disc 122 has a thickness of between about 1 mm and 8 mm. The converter may have two or more layers. A first layer may have a thickness of between about 0.5 mm and 4 mm. A second layer may have a thickness of between about 0.5 mm and 4 mm. The first layer may be comprised of a high Z material, such as tungsten, lead, or other high Z metal. The second layer may be comprised of a low or moderate Z material, such as aluminum copper, or the like. However, other materials may equally be used. The disc may receive incident electrons and convert them to photons (e.g., x-rays).

Collimator

Figure 19:
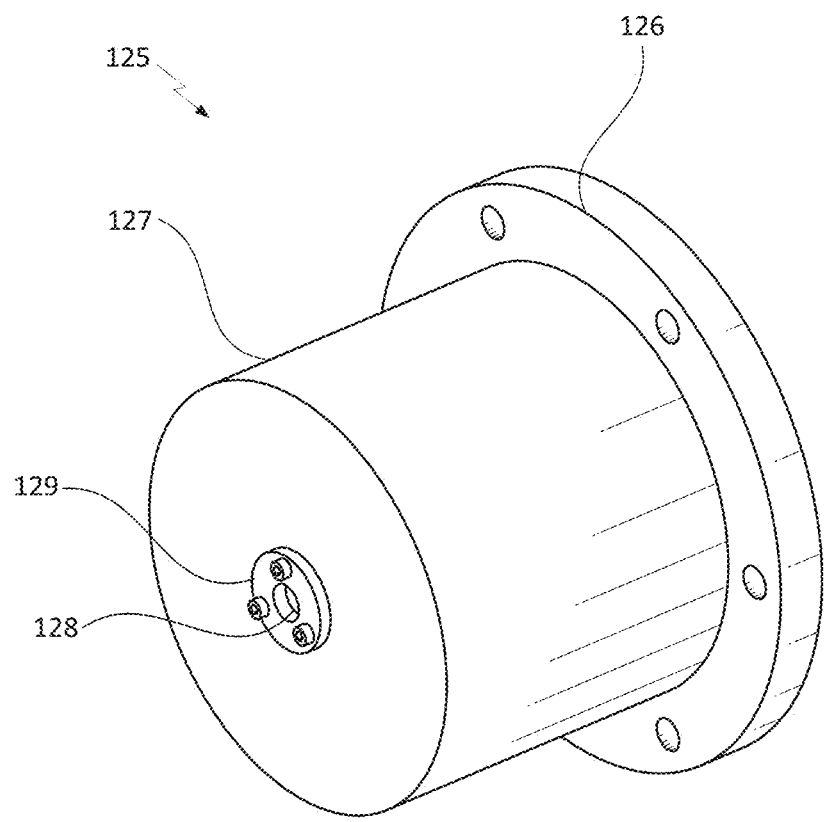
FIG. 19 is a perspective view of an example primary collimator for a linac waveguide.

FIG. 19 depicts an example collimator 125 for the photon beam produced at the converter as described above. A first collimator 125 may include a cylinder head 127 with a diameter of between about 80 mm and 130 mm. In some designs, the diameter of the cylinder head 127 is about 110 mm. In some embodiments, the cylinder head 127 is configured to reduce leakage of photons from the system, for example, to less than about 10 mGy/min at 1 m from the isocenter. A removable metal (e.g., tungsten) "plug" 129 may be provided which specifies the final field shape at aperture 128 and can be exchanged for other field sizes. In some embodiments, the plug 129 produces a rectangular field size having a length and/or width of up to 40 cm at 1 m from the converter.

Manufacturing

With continued reference to the drawings, various manufacturing considerations will now be described. In some implementations, individual cell components may be machined and cleaned. The cell components may then be joined with a brazing material and brazed (e.g., heated) to join the components together. The brazing material may comprise a material with a melting temperature lower than that of the material used in the cell components. The cell components may be made, for example, of metal such as copper. The brazing material may comprise an alloy, such as a copper alloy. In some embodiments, the brazing material comprises gold. Silver may also be used.

A first group of system components (e.g., cell components) may be brazed using a first brazing material. In some embodiments, the first brazing material includes an alloy. The first brazing material may be comprised of between about 50% and 90% of a first metal by weight. The first brazing material may be comprised of between about 10% and 50% of a second metal. The alloy metal has a lower melting then the cell material. The first group of system components may be brazed at a first brazing temperature. The first brazing temperature may be between about 900° C. and 1050° C.

A second group of system components may be brazed using a second brazing material. The second brazing material may be comprised of a lower percentage of the first metal by weight than the first brazing material. In some embodiments, the second brazing material includes a higher percentage of the second metal by weight than the first brazing material. The second brazing material may be comprised of between about 35% to 75% by weight of the first metal. The second brazing material may be comprised of between about 65% and 25% by weight of the second metal. Metals other than the first metal in second metal may be used for the second brazing material. The second group of system components may be brazed at a second brazing temperature. The second brazing temperature may be lower than the first brazing temperature. For example, the second brazing temperature may be between about 750° C. and 1050° C.

A third group of system components (e.g., water cooling plate(s)) may be brazed using a third brazing material. The third brazing material may be comprised of a lower percentage of the first metal by weight than the first brazing material and/or than the second brazing material. In some embodiments, the third brazing material includes a higher percentage of the second metal by weight than the first brazing material and/or than the second brazing material. The third brazing material may be comprised of between about 10% to 50% by weight of the first metal. The second brazing material may be comprised of between about 50% and 10% by weight of the second metal. Metals other than the first metal in second metal may be used for the third brazing material. The third group of system components may include one or more water cooling plates. The third group of system components may be brazed at a third brazing temperature. The third brazing temperature may be lower than the first brazing temperature and/or than the second brazing temperature. For example, the third brazing temperature may be between about 700° C. and 1000° C.

Treatment Systems

Figure 20:
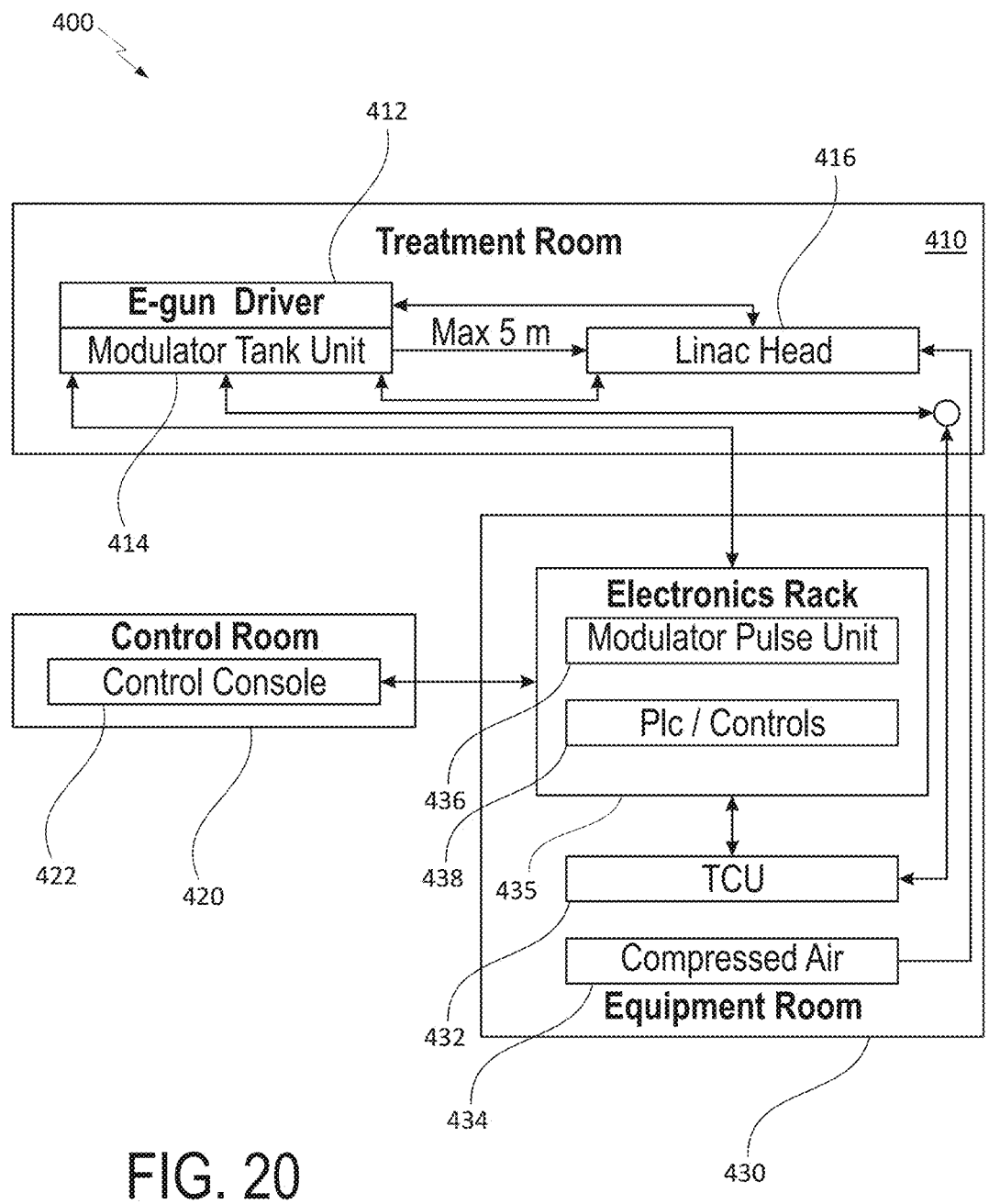
FIG. 20 schematically depicts an example treatment system configuration including the linac systems described herein.

These linear accelerator systems depicted herein and described above may work in conjunction to provide control signals, read back, power, and control interface to produce the required radiation parameters. FIG. 20 illustrates an example treatment system 400. The treatment system 400 generally includes a treatment room 410, a control room 420, and an equipment room 430. The treatment room may include a linac head 416, for example, including the various linac head components described above. The treatment room may further include an electron gun driver 412 and modulator tank unit 414. The control room 420 may include a control console 422. In some embodiments, a pulse transformer tank unit 436 is placed in the electronics rack 435 with the PLC/controls 438 or elsewhere outside the linac head 416, rather than in the linac head 416. Because the tank unit 436 may be large and/or heavy (e.g., 80 kg), it may be advantageous not to place the pulse transformer tank in the linac head 416. The equipment room 430 may also include a temperature control unit 432 and a compressed air supply 434. The temperature control unit 432 may be in fluid communication with the electronics rack 435, linac head 416, and/or modulator tank unit 414 by one or more coolant lines, such that the temperature control unit 432 can control the temperature of the coolant traveling to those components. The linac head 416 may be connected by control lines to the electron gun driver 412, and modulator tank unit 414. The electronics rack 435 may additionally be connected by one or more control lines to the control console 422 and/or the modulator tank unit 414.

Example Embodiments

1. A linear accelerator head for use in a medical radiation therapy system, the linear accelerator head comprising:
   a housing;
   an electron generator configured to emit electrons along a beam path;
   a microwave generation assembly comprising:
      a microwave generator configured to emit microwaves in a first direction along a primary wave path; and
      an isolator configured to prevent microwaves from propagating in a second direction opposite the first direction along the primary wave path;
   a waveguide configured to contain a standing or travelling microwave, the waveguide comprising:
      a plurality of cells disposed adjacent one another, wherein each of the plurality of cells defines an aperture configured to receive electrons therethrough, the aperture of the plurality of cells having a diameter and defining a beam axis of the waveguide along the beam path, wherein each of the plurality of cells has a first length defined along the beam axis;
      one or more bunching cells comprising an aperture configured to accelerate electrons therethrough, wherein each of the one or more bunching cells has a second length along the axis smaller than the first length of the plurality of cells; and
      a coupler cell configured to couple microwaves from the isolator into the waveguide;
      wherein the waveguide is configured to accelerate electrons to between about 3 MeV and 9 MeV;
   a cooling system in thermal communication with the waveguide;

a converter disposed within the electron beam path and configured to receive incident electrons, wherein the converter is configured to convert incident electrons into photons; and a first collimator configured to define a beam shape, wherein the first collimator comprises an input aperture and an output aperture;

wherein the linear accelerator head has a length of between about 50 cm and 120 cm, a width of between about 40 cm and 90 cm, and a depth of between about 20 cm and 75 cm.

2. The linear accelerator head of embodiment 1, wherein each of the plurality of cells comprises a cell wall with an attached tuner configured to deform the cell wall.

3. The linear accelerator head of embodiment 2, wherein the tuner is configured to allow a user to deform the cell wall by translating a portion of the cell wall radially toward the beam axis.

4. The linear accelerator head of any of embodiments 2-3, wherein the tuner is configured to allow the user to deform the cell wall by translating a portion of the cell wall radially away from the beam axis.

5. The linear accelerator head of any of embodiments 1-4, wherein the waveguide further comprises a plurality of side cells.

6. The linear accelerator head of embodiment 5, wherein each of the plurality of side cells comprises a tuner configured to allow a user to deform a side cell wall of the side cell by translating a portion of the side cell wall axially parallel to the beam axis.

7. The linear accelerator head of any of embodiments 5-6, wherein each of the plurality of side cells comprises an opening defining a shorting axis radial from the beam axis.

8. The linear accelerator head of any of embodiments 1-7, comprising an electron gun vacuum flange disposed between the electron generator and the waveguide, the electron gun vacuum flange comprising an electron gun vacuum flange aperture coaxial with the beam axis, wherein the electron gun vacuum flange is configured to provide fluid communication between a vacuum pump and an interior of the waveguide.

9. The linear accelerator head of any of embodiments 1-8, comprising a converter vacuum flange disposed between the waveguide and the converter, the converter flange comprising a converter vacuum flange aperture coaxial with the beam axis, wherein the converter vacuum flange is configured to provide fluid communication between a vacuum pump and an interior of the waveguide.

10. The linear accelerator head of any of embodiments 1-9, wherein the microwave generator comprises a magnetron.

11. The linear accelerator head of any of embodiments 1-10, wherein the microwave generator is configured to emit microwaves at a frequency in a range of between about 7.0 GHz and 11.2 GHz.

12. The linear accelerator head of any of embodiments 1-17, wherein the microwave generator is configured to emit waves at a power greater than 1 MW.

13. The linear accelerator head of any of embodiments 1-11 configured to deliver between about 300 cGy/min and 1,800 cGy/min.

14. The linear accelerator head of any of embodiments 1-13, wherein a means for attaching the electron generator to the waveguide comprises a removably coupled flange.

15. The linear accelerator head of any of embodiments 1-14 wherein the diameter of the aperture of each of the plurality of cells is between about 0.2 cm and 1.0 cm.

16. The linear accelerator head of any of embodiments 1-15, wherein the coupler cell is configured to provide fluid communication between a vacuum pump and an interior of the waveguide.

17. The linear accelerator head of any of embodiments 1-16, wherein the plurality of cells comprises fewer than 24 cells.

18. The linear accelerator head of any of embodiments 1-7, wherein the waveguide comprises a first exterior surface parallel to the beam axis.

19. The linear accelerator head of embodiment 18, wherein the waveguide comprises a second exterior surface, wherein the first exterior surface is parallel to the second exterior surface.

20. The linear accelerator head of any of embodiments 18-19, wherein the cooling system comprises a block defining a surface coplanar with the first exterior surface of the waveguide, the block comprising a channel configured to guide fluid therethrough.

21. The linear accelerator head of any of embodiments 18-20, wherein the cooling system comprises a block comprising a channel configured to guide fluid therethrough, wherein the block comprises an opening configured to allow a user access to at least one of the tuners of the plurality of cells.

22. The linear accelerator head of any of embodiments 1-21, wherein the converter comprises a disc comprising a first layer comprising a first material and a second layer comprising a second material.

23. The linear accelerator head of embodiment 22, wherein the first material comprises a chemical element having an atomic number greater than about 57.

24. The linear accelerator head of any of embodiments 22-23, wherein the second material comprises a chemical element having an atomic number lower than about 57.

25. The linear accelerator head of any of embodiments 22-24, wherein the first material comprises tungsten.

26. The linear accelerator head of any of embodiments 22-25, wherein the second material comprises aluminum.

27. The linear accelerator head of any of embodiments 22-25, wherein the second material comprises copper.

28. The linear accelerator head of any of embodiments 22-26, wherein the disc has a thickness of between about 1 mm and 8 mm.

29. The linear accelerator head of any of embodiments 22-28, wherein the first layer has a thickness of between about 0.5 mm and 4 mm.

30. The linear accelerator head of any of embodiments 22-29, wherein the second layer has a thickness of between about 0.5 mm and 4 mm.

31. The linear accelerator head of any of embodiments 1-30, wherein a diameter of a circle inscribed by the input aperture of the first collimator is greater than the diameter of the aperture of each of the plurality of cells.

32. The linear accelerator head of any one of embodiments 1-31, wherein a diameter of a circle inscribed by the output aperture of the first collimator is greater than the diameter of a circle inscribed by the input aperture.

33. The linear accelerator head of any of embodiments 1-32, further comprising a second collimator, wherein the second collimator comprises a plurality of collimating leaves.

34. The linear accelerator head of embodiment 33, wherein each of the plurality of collimating leaves is configured to translate along a collimating plane orthogonal to an axis defined by a circle inscribed by the output aperture.

35. The linear accelerator head of any of embodiments 33-34, wherein each of the plurality of collimating leaves comprises tungsten.

36. The linear accelerator head of any of embodiments 33-35, wherein each of the plurality of collimating leaves comprises lead.

37. A method of manufacturing a linear accelerator head for use in a medical radiation therapy system, the method comprising:
    assembling a waveguide comprising a plurality of cells, wherein each of the plurality of cells defines an aperture configured to receive electrons therethrough, the aperture of the plurality of cells having a diameter and defining a beam axis along a beam path, the step of assembling a plurality of cells comprising:
        for each of a first plurality of cells, providing a first brazing alloy between two adjacent cell members; and
        heating each of a first plurality of cells to a first brazing temperature;
    providing a housing;
    providing an electron generator configured to emit electrons along the beam path;
    providing a microwave generation assembly comprising:
        a microwave generator configured to emit microwaves in a first direction along a primary wave path; and
        an isolator configured to prevent microwaves from propagating in a second direction opposite the first direction along the primary wave path;
    providing a cooling system in thermal communication with the waveguide;
    providing a converter disposed within the electron beam path and configured to receive incident electrons, wherein the converter is configured to convert incident electrons into photons; and
    providing a first collimator configured to define a beam shape, wherein the first collimator comprises an input aperture and an output aperture.

38. The method of manufacturing a linear accelerator head of embodiment 37, wherein the step of assembling the plurality of cells comprises the step of for each of the first plurality of cells, machining a cavity into a portion of each of the two adjacent cell members.

39. The method of manufacturing a linear accelerator head of any of embodiments 37-38, wherein the first brazing alloy comprises between about 50% and 90% copper by weight.

40. The method of manufacturing a linear accelerator head of any of embodiments 37-39, wherein the first brazing alloy comprises between about 10% and 50% gold by weight.

41. The method of manufacturing a linear accelerator head of any of embodiments 37-40, wherein the first brazing temperature is between about 900° C. and 1100° C.

42. The method of manufacturing a linear accelerator head any of embodiments 37-41, wherein the step of assembling a plurality of cells comprises:
    for each of a second plurality of cells, providing a second brazing alloy between two adjacent cell members; and
    heating each of a second plurality of cells to a second brazing temperature.

43. The method of manufacturing a linear accelerator head of embodiment 42, wherein the step of assembling the plurality of cells comprises the step of for each of the first plurality of cells, machining a cavity into a portion of each of the two adjacent cell members.

44. The method of manufacturing a linear accelerator head of any of embodiments 42-43, wherein the second brazing alloy comprises between about 35% and 75% copper by weight.

45. The method of manufacturing a linear accelerator head of any of embodiments 42-44, wherein the second brazing alloy comprises between about 25% and 65% gold by weight.

46. The method of manufacturing a linear accelerator head of any of embodiments 44-45, wherein the second brazing alloy comprises a lower percentage by weight of copper than the first brazing alloy.

47. The method of manufacturing a linear accelerator head of any of embodiments 37-46, wherein the step of providing a cooling system in thermal communication with the waveguide comprises:
    providing a third brazing alloy between the waveguide and a cooling plate, the cooling plate comprising a channel configured to guide fluid therethrough; and
    heating the waveguide and cooling plate to a third brazing temperature.

48. The method of manufacturing a linear accelerator head of embodiment 47, wherein the third brazing temperature is between about 700° C. and 1000° C.

49. The method of manufacturing a linear accelerator head of any of embodiments 47-48, wherein the third brazing alloy comprises between about 10% and 50% copper by weight.

50. The method of manufacturing a linear accelerator head of any of embodiments 47-49, wherein the third brazing alloy comprises between about 50% and 10% gold by weight.

51. The method of manufacturing a linear accelerator head of any of embodiments 49-50, wherein the third brazing alloy comprises a lower percentage by weight of copper than the second brazing alloy.

52. The method of manufacturing a linear accelerator head of any of embodiments 37-51, further comprising the step of dipping the first plurality of cells into a solvent configured to dissolve oil.

53. The method of manufacturing a linear accelerator head of any of embodiments 3749-52, further comprising the step of propagating sound waves at ultrasound frequency at the first plurality of cells.

54. The method of manufacturing a linear accelerator head of any of embodiments 3749-50, further comprising the step of dipping the first plurality of cells into an etching solution configured to remove at least a layer of copper.

55. The method of manufacturing a linear accelerator head of embodiment 54, wherein dipping the first plurality of cells into an etching solution comprises dipping the first plurality of cells into the etching solution for a total time of at least fifteen seconds.

56. The method of manufacturing a linear accelerator head of any of embodiments 54-55, wherein the etching solution comprises phosphoric acid.

57. A system for delivering radiotherapy using a linear accelerator, the system comprising:
    a linear accelerator head of any of embodiments 1-36;
    a mechanical arm comprising a hinge defining a axis of rotation, the mechanical arm configured to rotate about the axis of rotation;
    wherein the linear accelerator head is mechanically coupled to the mechanical arm using a coupling device.

58. The system for delivering radiotherapy using a linear accelerator of embodiment 57, wherein the beam axis of the waveguide is perpendicular to the axis of rotation.

59. The system for delivering radiotherapy using a linear accelerator of any of embodiments 57-58, wherein one or more of a proximate end of the magnetic generator and a proximate end of the collimator is not disposed within about 15 cm from the axis of rotation.

60. The system for delivering radiotherapy using a linear accelerator of any of embodiments 57-59, wherein the coupling device is a hinge.

61. The system for delivering radiotherapy using a linear accelerator of any of embodiments 57-60, wherein an orientation between the linear accelerator head and the mechanical arm comprises a lower moment of inertia than an orientation wherein at least one of a proximate end of the magnetic generator and a proximate end of the collimator is within about 6 cm from the axis of rotation.

62. A compact linear accelerator head comprising:
an electron generator configured to emit electrons along a beam path;
a microwave generation assembly configured to emit microwaves in a first direction along a primary wave path;
a waveguide configured to contain a standing or travelling microwave and accelerate electrons to between about 3 MeV and about 9 MeV, the waveguide comprising:
a plurality of adjacent cells, each of the plurality of adjacent cells defining an aperture having a diameter and configured to receive electrons therethrough, the apertures of the adjacent cells defining a beam axis of the waveguide along the beam path, wherein each of the adjacent cells has a first length defined along the beam axis;
one or more bunching cells comprising an aperture configured to accelerate electrons therethrough, wherein each of the one or more bunching cells has a length along the beam axis smaller than the first length; and
a coupler cell configured to couple microwaves from the microwave generation assembly into the waveguide;
a converter disposed within the electron beam path, the converter configured to receive incident electrons and convert the incident electrons into photons, the converter comprising a disc comprising:
a first layer comprising a first material; and
a second layer comprising a second material; and
a first collimator configured to define a beam shape, wherein the first collimator comprises an input aperture and an output aperture.

63. A method of manufacturing a linear accelerator head, the method comprising:
assembling a waveguide comprising a plurality of cells, wherein each of the plurality of cells defines an aperture configured to receive electrons therethrough, the aperture of the plurality of cells having a diameter and defining a beam axis along a beam path, the step of assembling a plurality of cells comprising:
for each of a first plurality of cells, machining a cavity into a portion of each of the adjacent cell members;
for each of the first plurality of cells, providing a first brazing alloy between the two adjacent cell members; and
heating each of the first plurality of cells to a first brazing temperature;
providing an electron generator configured to emit electrons along the beam path;
providing a microwave generation assembly comprising:
a microwave generator configured to emit microwaves in a first direction along a primary wave path; and
an isolator configured to prevent microwaves from propagating in a second direction opposite the first direction along the primary wave path;
providing a cooling system in thermal communication with the waveguide;
providing a converter disposed within the electron beam path and configured to receive incident electrons, wherein the converter is configured to convert incident electrons into photons; and
providing a first collimator configured to define a beam shape, wherein the first collimator comprises an input aperture and an output aperture.

64. The method of claim 5, wherein the first brazing alloy comprises between about 50% and about 90% copper by weight.

65. The method of claim 5, wherein the first brazing alloy comprises between about 10% and about 50% gold by weight.

66. The method of claim 5A or 5B, further comprising dipping the first plurality of cells into an etching solution configured to remove at least a layer of copper.

67. The method of claim 5, further comprising dipping the first plurality of cells into an etching solution configured to remove at least a layer of a constituent element of the first brazing alloy.

68. The method of claim 5C or 5C1, wherein the first plurality of cells are dipped into the etching solution for a total time of at least thirty seconds.

69. The method of claim 5C, wherein the etching solution comprises phosphoric acid.

70. The method of claim 5, wherein the first brazing temperature is between about 900° C. and about 1100° C.

71. The method of claim 5, wherein providing the cooling system in thermal communication with the waveguide comprises:
providing a third brazing alloy between the waveguide and a cooling plate, the cooling plate comprising a channel configured to guide fluid therethrough; and
heating the waveguide and cooling plate to a third brazing temperature.

72. The method of claim 5, further comprising, subsequent to assembling the plurality of cells:
machining an opening into an exterior portion of at least one of the adjacent cell members, the opening extending inward toward the cavity of the cell member perpendicular to the beam axis; and
brazing a tuning stud in a location at least partially within the opening, the tuning stud configured to deform at least a portion of a cell wall of the cavity.

73. A system for delivering radiotherapy using a linear accelerator, the system comprising:
a compact linear accelerator head comprising:
an electron generator configured to emit electrons along a beam path;
a microwave generator configured to emit microwaves in a first direction along a primary wave path;
a waveguide configured to contain a standing or travelling microwave along a beam path and accelerate electrons to between about 3 MeV and about 9 MeV;
a cooling system in thermal communication with the waveguide;
a converter disposed within the electron beam path and configured to receive incident electrons and convert the incident electrons into photons;

a collimator configured to define a beam shape, the collimator comprising an input aperture and an output aperture; and a housing at least partially surrounding the electron generator, the microwave generator, the waveguide, the cooling system, the converter, and the collimator, wherein the housing has a length of between about 50 cm and about 120 cm, a width of between about 40 cm and about 90 cm, and a depth of between about 20 cm and about 75 cm; and a mechanical arm comprising a hinge defining an axis of rotation, the mechanical arm configured to rotate about the axis of rotation;

wherein the linear accelerator head is mechanically coupled to the mechanical arm by a coupling device, and wherein the beam axis of the waveguide is perpendicular to the axis of rotation of the mechanical arm.

74. The system of claim 6, wherein one or more of a proximate end of the microwave generator and a proximate end of the collimator is not disposed within about 15 cm from the axis of rotation.

Other Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended embodiments and/or claims and any equivalents thereof.

What is claimed is:

1. A compact linear accelerator head comprising:
an electron generator configured to emit electrons along a beam path;
a waveguide configured to contain a standing or travelling microwave and accelerate electrons to between about 3 MeV and about 9 MeV, the waveguide comprising a plurality of cells each defining an aperture configured to receive electrons therethrough along the beam path;
a microwave generator configured to produce microwave-range radiation;
a coupler positioned to couple the microwave-range radiation from the microwave generator into the waveguide; and
one or more vacuum ports disposed to provide fluid communication between a vacuum source and an interior of the waveguide.

2. The compact linear accelerator head of claim 1, wherein the waveguide is configured to receive the electrons from the electron generator at a first end of the waveguide and to accelerate the electrons along the beam path toward a second end of the waveguide opposite the first end.

3. The compact linear accelerator head of claim 2, wherein the one or more vacuum ports comprise:
a first vacuum port disposed at the first end of the waveguide; and
a second vacuum port disposed at the second end of the waveguide.

4. The compact linear accelerator head of claim 2, wherein the one or more vacuum ports comprise:
a first vacuum port disposed at the first end of the waveguide; and
a second vacuum port disposed at an intermediate location between the first end of the waveguide and the second end of the waveguide.

5. The compact linear accelerator head of claim 2, wherein the one or more vacuum ports comprise:
a first vacuum port disposed at the second end of the waveguide; and
a second vacuum port disposed at an intermediate location between the first end of the waveguide and the second end of the waveguide.

6. The compact linear accelerator head of claim 2, wherein the one or more vacuum ports comprise:
a first vacuum port disposed at the first end of the waveguide;
a second vacuum port disposed at the second end of the waveguide; and
a third vacuum port disposed at an intermediate location between the first end of the waveguide and the second end of the waveguide.

7. The compact linear accelerator head of claim 1, wherein a first one of the one or more vacuum ports comprises the coupler.

8. The compact linear accelerator head of claim 7, wherein a second one of the one or more vacuum ports comprises a first vacuum flange disposed at a first end of the waveguide between the waveguide and the electron generator or at a second end of the waveguide opposite the first end.

9. The compact linear accelerator head of claim 8, wherein the one or more vacuum ports further comprise a second vacuum flange disposed at the end of the waveguide opposite the first vacuum flange.

10. The compact linear accelerator head of claim 1, wherein a first one of the one or more vacuum ports comprises an electron gun vacuum flange disposed at a first end of the waveguide between the electron generator and the waveguide, the electron gun vacuum flange comprising a waveguide coupling section coaxial with a beam axis of the waveguide.

11. The compact linear accelerator head of claim 10, wherein a second one of the one or more vacuum ports comprises a vacuum flange disposed at a second end of the waveguide opposite the first end.

12. The compact linear accelerator head of claim 1, further comprising a converter disposed within the electron beam path and configured to receive incident electrons and convert the incident electrons into photons.

13. The compact linear accelerator head of claim 12, further comprising a converter vacuum flange disposed between the waveguide and the converter, the converter vacuum flange comprising a waveguide coupling section coaxial with the beam axis.

14. The compact linear accelerator head of claim 1, further comprising one or more vacuum pumps in fluid communication with the plurality of vacuum ports.

15. The compact linear accelerator head of claim 14, wherein the one or more vacuum pumps comprise a single vacuum pump in fluid communication with each of the one or more vacuum ports.

16. The compact linear accelerator head of claim 14, wherein the one or more vacuum pumps comprise a plurality of vacuum pumps, each of the plurality of vacuum pumps in fluid communication with a single one of the one or more vacuum ports.

17. The compact linear accelerator head of claim 1, wherein at least one of the one or more vacuum ports comprises a vacuum flange comprising:

a waveguide coupling section coaxial with the beam axis;
a vacuum pump coupling section disposed away from the beam axis; and
a waist extending radially away from the beam axis to provide fluid communication between the waveguide coupling section and the vacuum pump coupling section.

18. The compact linear accelerator head of claim 17, wherein the waveguide coupling section comprises:

an aperture coaxial with the beam axis;
an interior volume surrounding the aperture; and
a plurality of channels extending radially outward from the aperture to provide fluid communication between the aperture and the interior volume.

19. The compact linear accelerator head of claim 17, wherein the vacuum flange mechanically couples the waveguide to the electron generator.

20. The compact linear accelerator head of claim 17, wherein the vacuum flange mechanically couples the waveguide to a converter disposed an end of the waveguide along the beam path.

* * * * *